United States Patent
Okada et al.

[11] Patent Number: 6,129,735
[45] Date of Patent: Oct. 10, 2000

[54] ULTRASONIC TREATMENT APPLIANCE

[75] Inventors: Mitsumasa Okada, Hachioji; Makoto Miyawaki, Tanashi; Manabu Ishikawa, Hachioji, all of Japan

[73] Assignee: Olympus Optical Co., Ltd., Tokyo, Japan

[21] Appl. No.: 09/170,266

[22] Filed: Oct. 13, 1998

Related U.S. Application Data

[63] Continuation-in-part of application No. 08/878,574, Jun. 19, 1997, abandoned.

[30] Foreign Application Priority Data

| Jun. 21, 1996 | [JP] | Japan | 8-162041 |
| Nov. 5, 1996 | [JP] | Japan | 8-292802 |
| Oct. 15, 1997 | [JP] | Japan | 9-282098 |
| Oct. 28, 1997 | [JP] | Japan | 9-295070 |

[51] Int. Cl.$^7$ .................................................. A61B 17/32
[52] U.S. Cl. .............................................................. 606/169
[58] Field of Search ...................................... 606/169, 170, 606/171, 37, 39, 40, 45

[56] References Cited

U.S. PATENT DOCUMENTS

| 3,636,943 | 1/1972 | Balamuth | 128/24 |
| 5,322,055 | 6/1994 | Davison et al. | 601/2 |
| 5,501,698 | 3/1996 | Roth et al. | 606/205 |
| 5,658,300 | 8/1997 | Bito et al. | 606/143 |

FOREIGN PATENT DOCUMENTS

| 1-232948 | 9/1989 | Japan . |
| 5-95955 | 4/1993 | Japan . |
| 10-127654 | 5/1998 | Japan . |

*Primary Examiner*—Michael Buiz
*Assistant Examiner*—Vy Q. Bui
*Attorney, Agent, or Firm*—Armstrong, Westerman, Hattori, McLeland & Naughton

[57] ABSTRACT

An ultrasonic treatment appliance according to the present invention comprises a handpiece with a built-in ultrasonic transducer, and an elongated probe extending forward from the handpiece and connected to the ultrasonic transducer in order to propagate ultrasonic vibrations. The ultrasonic treatment appliance further comprises a distal probe part formed as an integral part of or independently of the probe at the distal end of the probe, a jaw opposed to the distal probe part so that the jaw can open or close freely, and a thin chip located on the jaw or, the clamping side of the clamping portion of the jaw on which the clamping portion touches a living tissue, or an elastic member interposed between the supporting portion and clamping portion of the jaw.

64 Claims, 15 Drawing Sheets

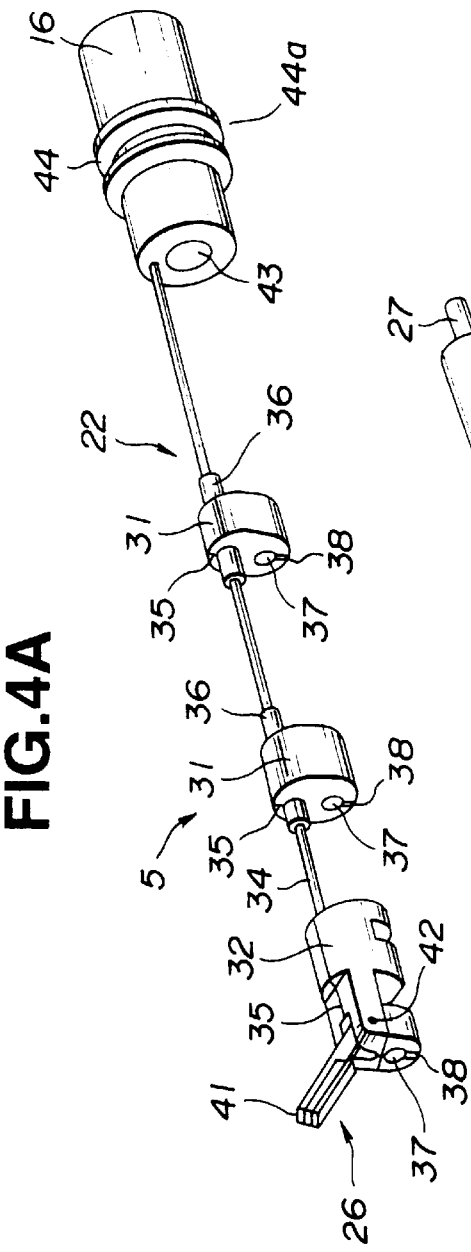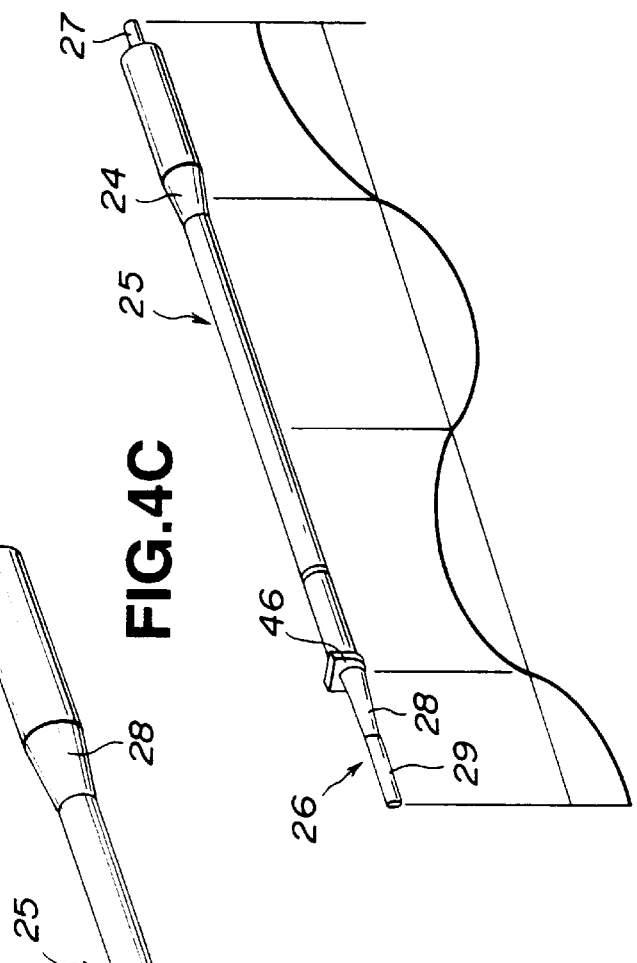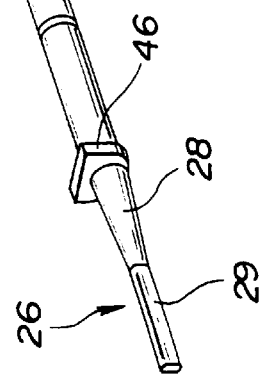

ULTRASONIC TREATMENT APPLIANCE

This application is a Continuation-in-part of prior application Ser. No. 08/878,574 filed Jun. 19, 1997 now abandoned.

BACKGROUND OF THE INVENTION

1. Field of the Invention

The present invention relates to an ultrasonic treatment appliance for incising, resecting, or coagulating a clamped region by propagating ultrasonic vibrations to a clamping portion that clamps a living tissue.

2. Description of the Related Art

In the past, an ultrasonic therapeutic appliance has been used to resect the prostate, crush calculi, or resect the liver. The ultrasonic therapeutic appliance is constructed by concatenating an ultrasonic transducer, horn, and vibration propagation member. Ultrasonic vibrations generated by the ultrasonic transducer are amplified mechanically by the horn, and transmitted to the vibration propagation member. The distal end of the ultrasonic propagation member and its surroundings are brought into contact with a living tissue of a lesion. The ultrasonic therapeutic appliance falls into an ultrasonic suction appliance having a pipe-like probe for emulsifying a tissue by utilizing ultrasonic vibrations, sucking a resultant tissue, and thus crushing and removing a lesion, and an ultrasonic coagulation/incision appliance having a scissors-like probe for coagulating or incising a tissue by utilizing heat derived from ultrasonic vibrations.

For example, the specification of U.S. Pat. No. 3,636,943 has disclosed a procedure of causing the tip of a probe to dissipate heat of a high temperature by applying ultrasonic vibrations to the probe serving as an ultrasonic treatment appliance, then resecting a living tissue and coagulating a bleeding region immediately at the same time, and thus effectively resecting a living tissue without causing bleeding. Japanese Unexamined Patent Publication No. 1-232948 has disclosed a treatment system configured to efficiently resect a living tissue by applying ultrasonic vibrations to a resection clamp. In the case of the treatment systems disclosed in the specification of the U.S. Pat. No. 3,636,943 and in the Japanese Unexamined Patent Publication No. 1-232948, the whole of a contact part that comes into contact with a living tissue during ultrasonic treatment is made of a metallic material.

The specification of U.S. Pat. No. 5,322,055 has presented an ultrasonic treatment appliance having a clamping member formed above the tip of a probe serving as a vibration propagation member, and conducting ultrasonic treatment while clamping and immobilizing a living tissue using the distal part of the probe and the clamping member. In this kind of ultrasonic treatment appliance, a soft contact member made of a plastic material is placed on a contact surface of a clamping member that comes into contact with a living tissue. The employment of the soft contact member prevents a noise from occurring when metallic clamping members meet during ultrasonic treatment.

The sharpness of the ultrasonic treatment appliance in resecting a living tissue is known to vary depending on the frequency of ultrasonic vibrations. For example, when a relatively low frequency is selected as a frequency to be set in an ultrasonic transducer, a distance of the position of a node in a probe which acts as a fulcrum of a clamping member for clamping a living tissue from the tip of the probe acting as a working point of the clamping member gets larger. The probe is therefore likely to deflect when a load is applied by the clamping member. When the clamping member is used to clamp a living tissue, force exerted to clamp the living tissue weakens. The living tissue cannot therefore be clamped reliably and may come off from the clamping member. As a result, the work of resecting the living tissue becomes hard to do. This poses a problem of deteriorated workability.

As described in the specification of the U.S. Pat. No. 5,322,055, when a clamping member made of a resin material such as so-called Teflon is employed, when the clamping member clamping a living tissue is highly heated by propagated ultrasonic vibrations, the clamping member may be deformed due to the heat. If the clamping member is thermally deformed, force exerted to clamp a living tissue weakens. Consequently, the living tissue cannot be clamped reliably and may come off from the clamping member. As a result, the work of resecting the living tissue becomes hard to do. This poses a problem of deteriorated workability.

Furthermore, the width of a clamping member for clamping a living tissue in cooperation with the distal part of an ultrasonic probe must, in principle, be considerably small so that the clamped state can be readily discerned by an endoscope. If the clamping member is made of a resin material such as so-called Teflon and is thin, the resin clamping member is liable to be damaged, that is, deformed, melted to be burnt, or worn out because of heat generated during ultrasonic treatment and clamping force. Even if the clamping member is made thick, the resin material is inferior in durability to metals or the like from both thermal and mechanical viewpoints. Even if the thickness of a clamping member made of a resin material were increased, durability would not drastically improve.

As mentioned above, a clamping member made of a resin material is inferior in durability to any metallic clamping member from both thermal and mechanical viewpoints. This poses a problem that ultrasonic treatment cannot be conducted with high power and treatment efficiency is hard to improve. In an effort to solve this problem, it is conceivable to produce a clamping member using a metallic member. In this case, the problem of the thermal and mechanical inferiorities of the clamping member made of a resin material can be solved but a problem described below arises newly.

The instant a living tissue clamped by the distal part of an ultrasonic probe is incised perfectly, the vibrating distal part of the probe comes into contact with the surface of a clamping member formed with a metallic member. This results in a violent loud mechanical sound. This phenomenon is presumably attributable to the fact that since the probe for propagating ultrasonic vibrations is elongated, vibrations including ultrasonic vibrations as well as complex vibrations such as rolling occur in the distal part, and as a result, a hit sound occurs at the distal end of the metallic clamping member.

Moreover, when the ultrasonic suction appliance is in use, the vibration propagation member may receive an extraneous force oriented in a lateral direction when meeting an object or the like. In this case, the probe that is the vibration propagation member meets a coaxial sheath fitted on the outer circumference of the probe with a certain distance between them. Consequently, the meeting portion of the vibration propagation member is worn out. Otherwise, in the case of the ultrasonic coagulation/incision appliance, friction occurs between the vibration propagation member structured as one of blades of scissors and a clamping member structured as the other blade thereof and designed not to vibrate ultrasonically. The friction results in abrasion.

As a method of preventing the abrasion that results from friction, Japanese Unexamined Patent Publication No. 5-95955 has disclosed a technology for hardening the surface of the vibration propagation member. According to the technology, the surface of a titanium alloy normally made into the vibration propagation member is coated by performing physical-vapor deposition (PVD) such as ion plating or chemical-vapor deposition (CVD).

According to the CVD, coating is carried out under a high-temperature environment. A coating is attached closely to a base material. However, the phase of the base material is affected. This causes the properties of the titanium alloy that is the base material to change. The performance of transmission of ultrasonic waves is reportedly affected adversely. For this reason, an actually adopted coating method is the PVD.

However, if the PVD were adopted for coating, a coating layer would be a film whose thickness is limited to about 3 $\mu$m cost-wise. When the vibration propagation member and sheath meet for a long period of time as mentioned previously, the coating of the thin film would readily be worn away and the base material would be exposed. Consequently, an internal stress and bending stress stemming from applied ultrasonic vibrations are concentrated on the abraded portion of the vibration propagation member. If ultrasonic vibrations are kept applied to the portion, the vibration propagation member comes to a limit of endurance against a fatigue failure. An initial crack develops in the abraded portion, thus leading to the fatigue failure. Although the coating is as thin as 3 $\mu$m in thickness, the Vickers hardness of the coating is approximately 1200. By contrast, the Vickers hardness of the titanium alloy that is the base material is approximately 600. For example, when a strong impact is imposed on the surface of the coating on the vibration propagation member, even if the coating is free from any damage, the impact is imposed on the base material. Consequently, the base material may crack. In this case, the base material under the coating layer a flaw may be flawed, and stresses may be concentrated on the flaw during transmission of ultrasonic waves. This brings about a factor of causing an initial crack leading to a breakage.

Moreover, an ultrasonic treatment appliance may be used to coagulate or cut away a large region of a tissue that is relatively hard to cut away, for example, the liver or duodenum. For this purpose, a large clamping force is needed.

In this case, a large bending stress is induced in a probe. The bending stress causes the probe to warp in a direction in which the claming member is closed, that is, a direction opposite to a direction in which the clamping member is located. Generally, the clamping member is designed to press the whole probe with the same load. When an object is clamped, a uniform load is applied to the probe.

At this time, the bending stress induced in the probe depends greatly on the sectional shape of the clamping portion of the probe, that is, the section modulus thereof.

Currently, as presented in the U.S. Pat. No. 5,322,055, the cross sectional shape of the clamping portion of a probe is fixed to a certain shape in the direction of the length thereof.

Now, actual treatment will be discussed.

As the diameter of a probe is smaller, a field of view provided near the tip of the probe is wider. This permits delicate treating manipulation. However, since the probe is shaped so that the section modulus is small for a normal stress in the probe. The probe therefore warps.

Moreover, the outer diameter of the insertion unit of the aforesaid existing handpiece is approximately 10 mm. If the handpiece is designed compactly to have an outer diameter of 5 mm or 3 mm, the sectional area of the probe must be made smaller than the existing one. At this time, the probe exhibits a small section modulus for a normal stress required for coagulating or cutting away a tissue.

Assume that a probe has a shape like the existing shape enabling the probe to exhibit a constant section modulus, which is smaller than a certain value, over the distal part of the probe. In this case, when a quantity of clamping force that is a normal stress increases, the probe may warp.

When the probe cooperates with the clamping member warps in clamping a tissue, if the probe warps, the probe and clamping member do not fully mesh with each other. In other words, the roots of the probe and clamping member have such a positional relationship that a tissue is attached closely to the roots and cannot therefore be coagulated or cut away. The tips thereof have such a positional relationship that they are spaced enough to coagulate or cut away a tissue. This leads to a problem that the ability to resect a tissue deteriorates.

Moreover, an operator may manipulate the ultrasonic treatment appliance to limit the movements of the clamping member in an effort to reduce a quantity of clamping force. The operator intends to prevent the probe from warping to have the positional relationship that disables coagulation or cutting. As a result, the quantity of clamping force becomes too small. This poses the problem of the deteriorated ability to resect a tissue.

Furthermore, there is another problem that a probe, or especially, the upper side of the probe is prone to flaws.

For example, an incorrect treatment appliance may be grabbed by mistake during ultrasonic oscillation within an actual surgical procedure. In this case, it is unavoidable that the upper side of the probe is flawed even slightly.

Moreover, a burnt tissue sticking to the upper side of the probe may be washed away during cleaning after use. When the upper side of the probe is scrubbed using a sharp cleaning tool, the probe may be flawed.

Moreover, similarly to an ultrasonic treatment appliance disclosed in the Japanese Unexamined Patent Publication No. 10-127654, some ultrasonic treatment appliances have a metallic probe mated with a clamping member. Every time the probe is vibrated ultrasonically, the probe rubs against the clamping member. The probe may then be flawed.

It can be said that the aforesaid ultrasonic treatment appliances are structured so that the upper side of each probe and its surroundings are prone to a flaw, that is, a small crack.

Assume that a living tissue is clamped and the probe is vibrated ultrasonically with a small crack created on the upper side of the probe. A stress distribution is a compound of stresses induced by ultrasonically vibrating the probe (in this case, generally, a maximal stress is observed at nodes of ultrasonic vibrations and a minimal stress is observed at antinodes thereof), and a bending stress induced in the probe due to clamping. The stresses act on the flaw on the upper side of the probe. At this time, the bending stress induced by claming a tissue works as a load stress causing the flaw on the upper side of the probe to expand. In this state, when the probe is vibrated repeatedly, a fatigue crack may develop with the flaw as an origin.

OBJECTS AND SUMMARY OF THE INVENTION

The first object of the present invention is to provide an ultrasonic treatment appliance making it possible to minimize occurrence of a noise caused by a clamping member that vibrates due to propagated ultrasonic waves, and to improve resection and coagulation abilities.

The second object of the present invention is to provide an ultrasonic treatment appliance making it possible to prevent deterioration of resection and coagulation abilities caused by heat stemming from ultrasonic vibrations and to maintain the durability of a clamping member.

The third object of the present invention is to provide an ultrasonic treatment appliance capable of exerting a sufficient quantity of clamping force at the time of clamping a living tissue using a clamping member, eliminating the fear that the living tissue may come off from the clamping member, clamping the living tissue reliably, and offering improved resection and coagulation abilities.

The fourth object of the present invention is to provide an ultrasonic treatment appliance having a vibration propagation member that exhibits excellent abrasion resistivity and sufficient strength.

The fifth object of the present invention is to provide an ultrasonic treatment appliance capable of suppressing a magnitude of warp of a probe occurring when the probe is used to clamp a living tissue, maintaining the ability to coagulate or resect the tissue on a stable basis, and improving the durability and strength of the probe.

Briefly, an ultrasonic treatment appliance of the present invention comprises a handpiece with a built-in ultrasonic transducer, and an elongated probe extending forward from the handpiece and connected to the ultrasonic transducer in order to propagate ultrasonic vibrations. The ultrasonic treatment appliance further comprises a distal probe part formed as an integral part of or independently of the probe at the distal end of the probe, a jaw opposed to the distal probe part so that the jaw can open or close freely, and an auxiliary member, included in the jaw, for minimizing a sound stemming from vibrations propagated from the distal probe part.

The auxiliary member is a thin chip located on the clamping side of the jaw on which the jaw touches a living tissue, a thin chip located on the clamping side of a clamping portion of the jaw on which the clamping portion touches a living tissue, or an elastic member interposed between a supporting portion of the jaw and the clamping portion thereof.

BRIEF DESCRIPTION OF THE DRAWINGS

FIGS. 1 to 9 are diagrams for explaining the first embodiment of the present invention;

FIG. 1 is an oblique view of an ultrasonic incision/coagulation appliance;

FIG. 2 is an oblique view separately showing a main unit of a handpiece of an ultrasonic incision/coagulation appliance and a treatment unit thereof;

FIG. 3 is a diagram showing an example of a sectional shape of a distal probe part;

FIG. 4A is an oblique view for explaining the treatment unit;

FIG. 4B is an oblique view for explaining the probe;

FIG. 4C is a view showing positions in the probe coincident with nodes of ultrasonic vibrations;

FIG. 6 is a diagram showing the treatment assembly from the tip thereof;

FIG. 7 is a diagram showing the positional relationship between a thin chip and the distal probe part;

FIG. 8 is an oblique view for explaining the treatment assembly having the thin chip in a jaw body;

FIG. 9 is an oblique view for explaining the positional relationship between the jaw body and thin chip;

FIG. 10A is a diagram showing the structure of a probe;

FIG. 10B is a diagram showing a state in which the distal probe part is screwed to the probe;

FIG. 10C is a diagram showing another structure of a probe;

FIG. 17 is an oblique view showing another structure including a clamping portion and supporting portion;

FIG. 18 is an oblique view showing a state in which the clamping portion is fixed to the supporting portion;

FIG. 19 is an oblique view showing a jaw constructed by interposing a rubber member as an elastic member between a clamping portion and supporting portion;

FIG. 20 is a view showing a clamping portion and elastic member which are formed in one united body and attachable to or detachable from a supporting portion;

FIG. 24 is a sectional view showing the structure of a distal probe part;

FIG. 25 is a diagram for explaining a stress distribution over coatings employed in the eighth embodiment;

FIG. 29 is a longitudinal sectional view of the distal part of an ultrasonic incision/coagulation appliance and its surroundings with a clamping member unit and probe assembled, showing the distal probe part;

FIG. 30 is a front view of the distal part of the ultrasonic incision/coagulation appliance and its surroundings;

FIG. 31 is a longitudinal sectional view of a clamping member of the ultrasonic incision/coagulation appliance;

DESCRIPTION OF THE PREFERRED EMBODIMENTS

Referring to FIGS. 1 to 9, the first embodiment of the present invention will be described.

In this embodiment, an ultrasonic incision/coagulation appliance is taken as an example of an ultrasonic treatment appliance.

Figure 1:
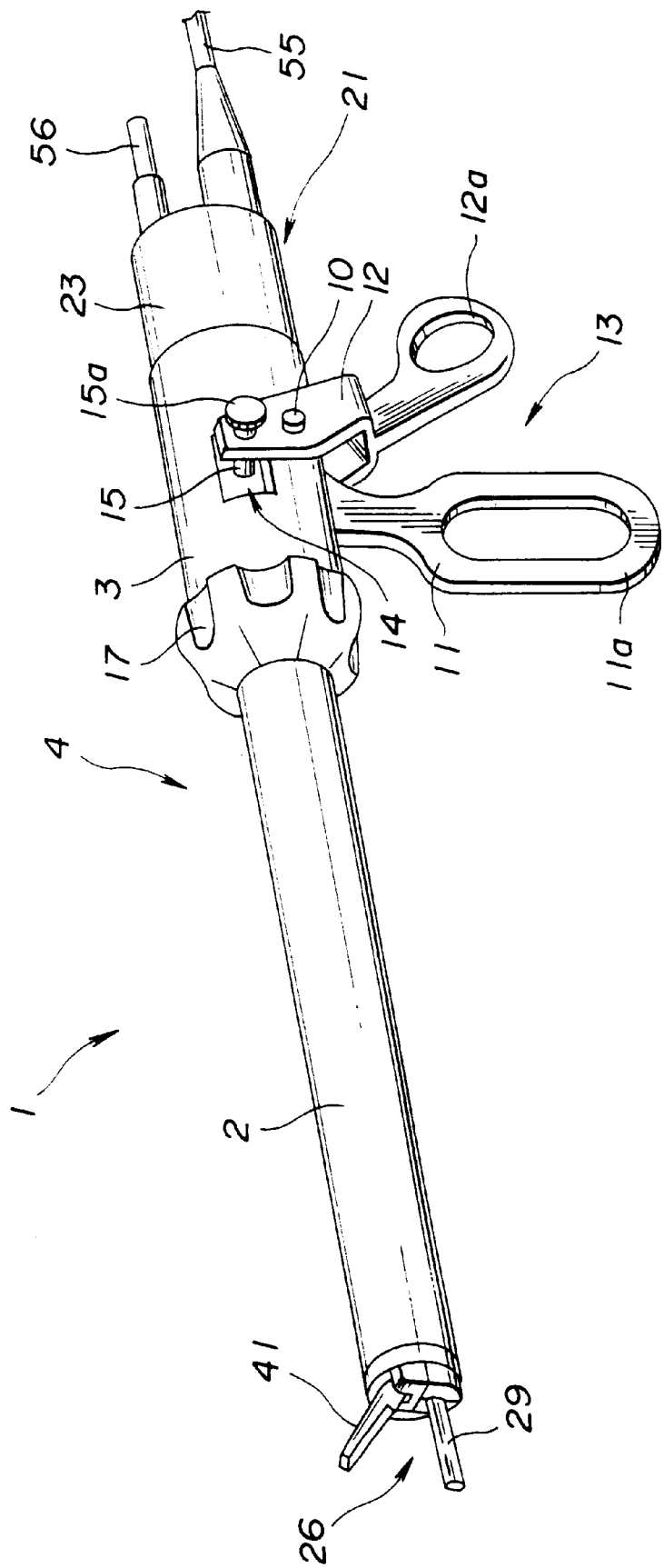

As shown in FIG. 1, an ultrasonic incision/coagulation appliance 1 has a main unit of a handpiece (main unit of a treatment appliance) 4 including an elongated cylindrical sheath 2 that is an insertion unit protecting member and a cylindrical grip sheath 3 located proximally to the sheath 2. A treatment unit 5 is mounted in the main unit 4 so that the treatment unit 5 can be dismounted freely (See FIG. 2).

The grip sheath 3 includes an operation unit 13 composed of a stationary handle 11 and movable operation handle 12. The stationary handle 11 is fixed to the grip sheath 3, while the movable operation handle 12 is attached to the grip sheath 3 by a pin 10 so that the movable operation handle 12 can pivot freely. The movable operation handle 12 can therefore pivot freely relative to the stationary handle 11. The stationary handle 11 and movable operation handle 12 have finger rest rings 11a and 12a respectively.

A window 14 is formed on one side surface of the grip sheath 3. A stoppage pin (or stopper) 15 located at the upper edge of the movable operation handle 12 is inserted into the window 14. The stoppage pin 15 is fitted into an annular groove 44a (See FIG. 4A) formed in a sliding cylinder 16 included in the treatment unit 5. By manipulating the movable operation handle 12 of the operation unit 13, the sliding cylinder 16 is slided in distal and proximal directions. This causes a jaw 41 serving as a treatment clamping member that is a constituent part of an ultrasonic treatment assembly 26, which will be described later, to freely open or close relative to a distal probe part 29.

The stoppage pin 15 is screwed and fixed to the upper edge of the movable operation handle 12, and can therefore be advanced or withdrawn by rotating a head 15a of the stoppage pin 15. Specifically, the stoppage pin 15 may be moved to the annular groove 44a of the sliding cylinder 16 so that the tip of the stoppage pin 15 is fitted into the annular groove 44a. Alternatively, the stoppage pin 15 may be moved in an opposite direction so that the tip of the stoppage pin 15 withdraws from the annular groove 44a. Thus, the stoppage pin 15 may be released from the fitted state into the annular groove 44a.

The proximal part of the sheath 2 is attached to the grip sheath 3 so that the sheath 2 can be rotated freely about the axis thereof. The sheath 2 can therefore be rotated about the axis thereof by holding and rotating a rotation knob 17 put on the proximal part of the sheath 2. Also shown in FIG. 1 are an ultrasound drive power cord 55 and a power cord 56 to be connected with a power source for high-frequency treatment.

Figure 2:
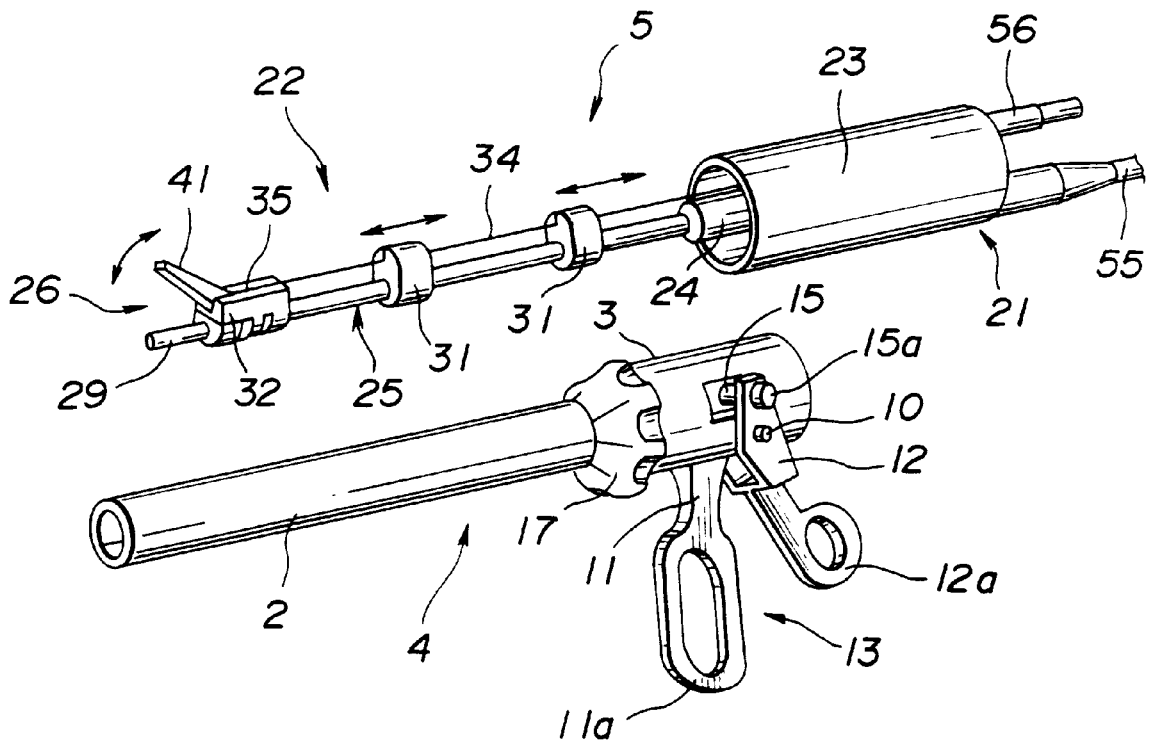

As shown in FIG. 2, when the main unit 4 is detached from the grip sheath 3, a treatment unit 5 composed of an ultrasonic transducer unit 21 and clamping member unit 22 becomes visible.

The ultrasonic transducer unit 21 consists mainly of an ultrasonic transducer, which is not shown, incorporated on a fixed basis in a cover sheath 23 of the handpiece, a horn 24 located distally to the ultrasonic transducer, and a probe 25 serving as a vibration propagation member for propagating ultrasonic vibrations generated by the ultrasonic transducer. Ultrasonic vibrations generated by the ultrasonic transducer are expanded by the horn 24 and propagated to the distal probe part 29 that is a constituent part of the ultrasonic treatment assembly 26. The horn 24 for propagating vibrations generated by the ultrasonic transducer and the probe 25 are made of a titanium or aluminum material, which is characteristic of excellent sound effects and well acceptable to a living body, or an alloy thereof.

As shown in FIG. 4B, the probe 25 is screwed to the horn 24 located distally to the ultrasonic transducer by means of a male screw 27 located at the proximal end of the probe 25. The probe 25 is formed with a solid straight rod devoid of a small-diameter portion such as a step or ditch, though it has a tapered horn portion 28 in the middle thereof. The probe 25 is therefore highly rigid. The distal probe part 29 having a small diameter is formed as the extreme distal part of the probe 25. The distal probe part 29 serves as a stationary cutter of the ultrasonic treatment assembly 26.

Figure 3:
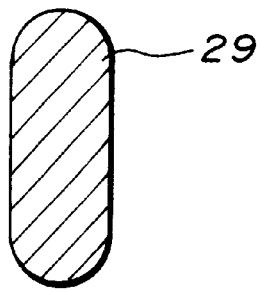

The sectional shape of the distal probe part 29 is not limited to a circle. For improving treatment efficiency and designing a treatment working portion compactly, as shown in FIG. 3, the width of the cutter may be narrowed and a circular blade may be formed on the upper and lower sides of the distal probe part. Otherwise, an elliptic blade or triangular blade which is not shown may be formed thereon. For well-balancing the operation of incision and that of coagulation, cutters having various forms are used as the distal probe part.

The clamping member unit 22 shown in FIG. 2 consists mainly of the jaw 41 opposed to the distal probe part 29 so that the jaw 41 can open or close freely as indicated with arrows, a plurality of spacers 31 arranged at positions on the probe 25 coincident with nodes of ultrasonic vibrations, and an elongated operation rod 34 serving as an operation force conveying medium member to be coupled with the jaw 41. A spacer located extremely distally among all the plurality of spacers 31 also acts as a jaw supporting base, and shall be referred to as a distal spacer 32 distinguishably from the spacers 31. The jaw 41 serves as a movable cutter of the ultrasonic treatment assembly 26.

As shown in FIG. 4A, ditches 35 are formed in the upper parts of the spacers 31 so that the operation rod 34 can be fitted into the ditches 35. Outer locking members 36 that are small-diameter pipes are put in the ditches 35 bored in the spacers 31. The operation rod 34 is run through the bores of the outer locking members 36, whereby the operation rod 34 is fixed to the spacers 31. The outer locking members 36 are fitted into and fixed to the ditches 35 of the spacers 31.

The operation rod 34 is fixed to the spacers 31 except the distal spacer 32 located extremely distally as integral parts of the spacers 31. When the operation rod 34 is advanced or withdrawn in a longitudinal direction within the sheath 2, the spacers 31 move within the sheath 2 along with the movement of the operation rod 34.

However, the spacers 31 should, in principle, merely be held by the operation rod 34 without being displaced from the positions on the probe 25 coincident with the nodes (See FIG. 4C) of ultrasonic vibrations. The spacers 31 and operation rod 34 may be fixed to each other directly or via the outer locking members 36. As long as the spacers 31 will not be displaced from the positions coincident with the nodes of ultrasonic vibrations, the spacers 31 may not be fixed to the operation rod 34 but may merely be held thereby.

In this embodiment, since the spacers 31 are positioned on and fixed to the operation rod 34 using the outer locking members 36, it becomes unnecessary to machine the probe 25 so as to create irregular parts for use in positioning the spacers 31. This results in the simplified structure of the probe 25 and reduced cost. Moreover, the strength of the probe 25 is improved.

In the lower part of each spacer 31, a through hole 37 in which the probe 25 is loosely inserted, and an attachment/detachment slit 38 used to introduce the probe 25 to the through hole 37 are bored. The probe 25 is inserted into the through holes 37 so that the probe can slide freely in an axial direction. In an effort to facilitate the sliding efficiency of the probe 25, the spacers 31 are made of a fluorocarbon resin material characteristic of high sliding efficiency, such as, so-called Teflon.

Figure 5A:
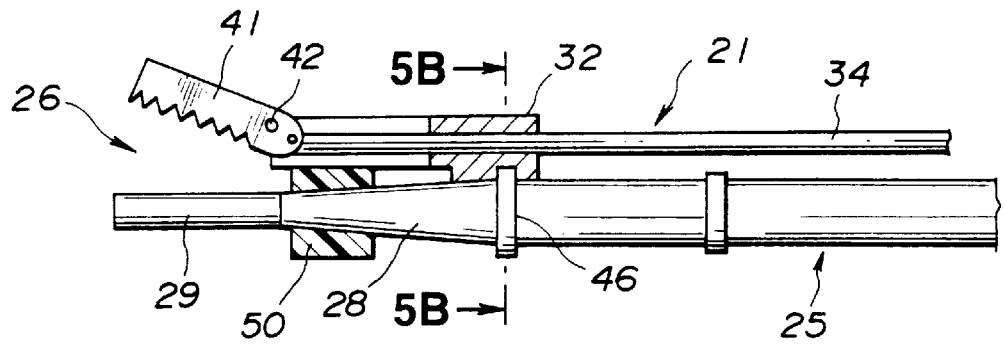
FIG. 5A is a diagram for explaining a treatment assembly and distal spacer.

As shown in FIG. 4A, the jaw 41 that is a metallic clamping member for clamping or freeing a living tissue in cooperation with the distal probe part 29 while being opposed to the distal probe part 29 is attached to the distal spacer 32 located extremely distally using a pin 42 so that the jaw 41 can pivot freely. As shown in FIG. 5A, the tip of the operation rod 34 is coupled with the proximal end of the jaw 41.

As shown in FIG. 4A, the proximal end of the operation rod 34 is coupled with the sliding cylinder 16. The sliding cylinder 16 has an insertion bore 43 into which the probe 25 is inserted. On the outer circumference of the sliding cylinder 16, juts 44 defining the annular groove 44a into which the stoppage pin 15 of the movable operation handle 12 is fitted are formed.

The sliding cylinder 16 is put in the grip sheath 3 so that the sliding cylinder can slide freely. The sliding cylinder 16 is therefore advanced or withdrawn in a longitudinal direction within the grip sheath 3 by turning the movable operation handle 12 relative to the stationary handle 11. This causes the operation rod 34 coupled with the sliding cylinder 16 to advance or withdraw in the longitudinal direction. The jaw 41 opposed to the distal probe part 29 then opens or closes.

The distal spacer 32 supporting the jaw 41 coincides with an extremely distal node (See FIG. 4C) of ultrasonic vibrations propagating along the probe 25 that is a vibration propagation member, and supports the probe 25 in a non-rotated state. As shown in FIG. 4C, for example, a rectangular flange 46 is formed at the extremely distal position on the probe 25 coincident with the node of ultrasonic vibrations.

Figure 5B:
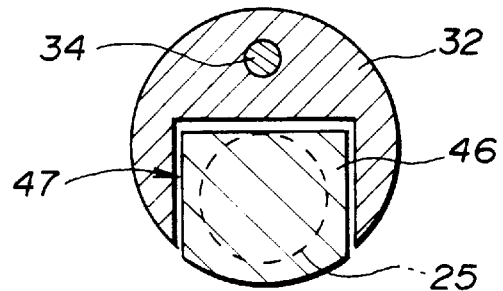
FIG. 5B is a 5B—5B sectional diagram of FIG. 5A.

As shown in FIGS. 5A and 5B, the flange 46 is locked in an engagement ditch 47 bored in the lower surface of the distal spacer 32 in line with the contour of the flange 46. The probe 25 is therefore held by the distal spacer 32 in a state in which the probe 25 cannot rotate. The probe 25 and distal spacer 32 are incorporated in the sheath 2 so that they rotate about the axes thereof in unison. The orientation of the distal probe part 29 relative to the jaw 41 is therefore constant all the time. The upper side of the distal probe part 29 is thus restricted to always face the clamping side of the jaw 41.

Figure 6:
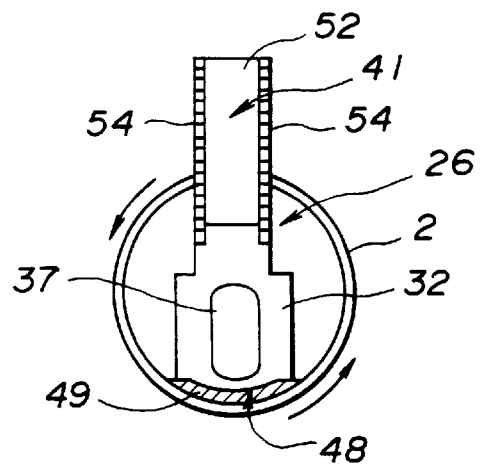

As shown in FIG. 6, the lower surface of the distal spacer 32 is formed as a substantially flat locking end surface 48. The locking end surface 48 is locked by a detent member 49 fixed to the inner surface of the sheath 32. This realizes a detent for hindering the distal spacer 32 from rotating about the axis thereof within the sheath 2.

A bracing member 50 made of a material permitting smooth sliding, such as, so-called Teflon is included in the distal spacer 32 as an integral part of the distal spacer 32 in an effort to prevent the distal probe part 29 from swinging. The bracing member 50 holds the horn portion 28 formed in the distal portion of the probe 25 so as to prevent deflection.

Figure 7:
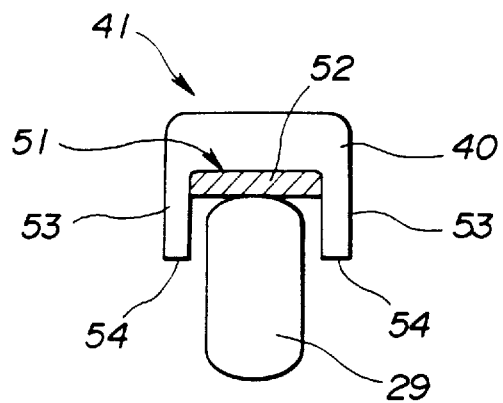
Figure 8:
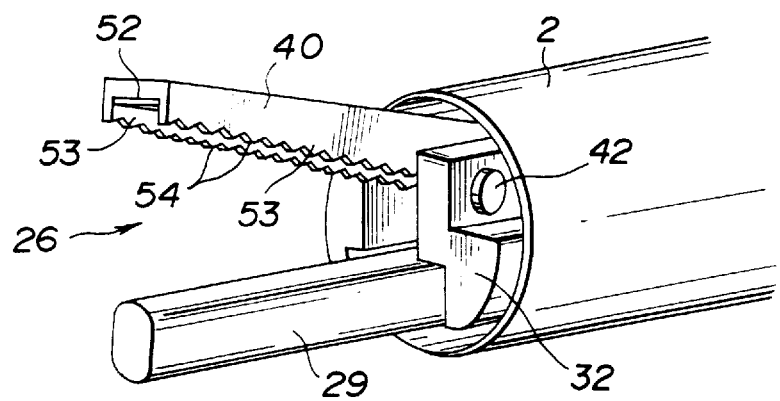
Figure 9:
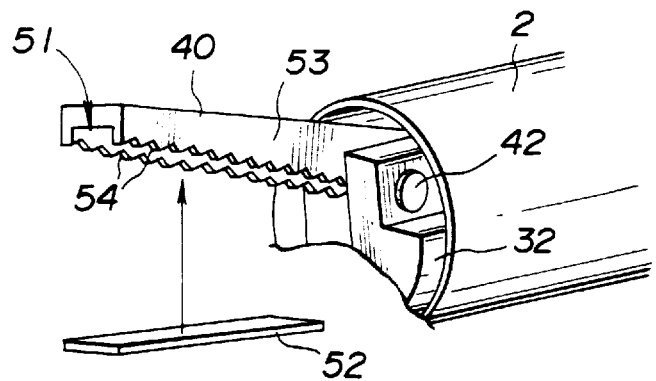

Referring to FIGS. 7 to 9, the detailed structure of the jaw 41 will be described.

As shown in FIGS. 7 and 8, the jaw 41 is composed of a jaw body 40 having a clamping ditch 51 that provides a clamping surface in a longitudinal direction, and jutting rims 53 located on both margins of the clamping ditch 51, and a thin chip 52 placed on the bottom of the clamping ditch 51 of the jaw body 40, serving as an auxiliary member for minimizing a sound stemming from contact with the distal probe part 29, and made of stainless steel or a ceramic material.

As shown in FIGS. 8 and 9, a plurality of triangular teeth 54 are formed on the jutting rims 53 on the clamping sides of the jutting rims 53. Since the triangular teeth 54 are formed on the jutting rims 53, when a living tissue is clamped by the jaw 41 and distal probe part 29, the living tissue can be caught reliably.

The thickness of the thin chip 52 ranges from 0.05 mm to 0.5 mm, or preferably, ranges from 0.1 mm to 0.3 mm. This is attributable to the fact that the smaller the thickness is, the smaller the volume of a sound occurring when the clamping surface of the thin chip 52 that is a plane on a treatment side of the thin chip comes into contact, as shown in FIG. 7, with the upper surface of the distal probe part 29 is. The fact is confirmed experimentally, too.

However, when the thickness of the thin chip 52 is set to, for example, 0.05 mm or less, there arises a problem in durability. By contrast, when the thickness thereof is set to, for example, 0.5 mm or more, the volume of a sound becomes considerably large. When an attempt is made to set the thickness of the thin chip 52 within the above range, the trade-off between the volume and durability depends on user's likes. Specifically, when a small volume is desired despite little poor durability, the jaw 41 having the thin chip 52 of 0.2 mm in thickness is employed.

The width of the thin chip 52 is substantially the same as that of the clamping ditch 51. As for the length thereof, the thin chip 52 is set to a length enabling the whole of the treatment portion of the distal probe part 29 to abut on the thin chip.

As shown in FIG. 9, in this embodiment, when the thin chip 52 is put in the clamping ditch 51, an adhesive is used to lock the thin chip 52. However, a means for locking the thin chip 52 in the clamping ditch 52 is not limited to the adhesive but may be any other means such as snap fitting, spot welding, or laser point welding.

For fixing the thin chip 52 to the jaw body 40 by performing welding, it is essential that the jaw body 40 and thin chip 52 should not be united in terms of sound effects. Welding points should therefore be near the right-hand and left-hand margins of the thin chip 52, while welding the surface of the thin chip with which the distal probe part 29 comes into contact should be avoided.

The clamping surface of the thin chip 52, and the surface of the distal probe part 29 coming into contact with the clamping surface are polished to be smoothened. This is intended to suppress occurrence of frictional heat and a frictional sound.

Moreover, the clamping surface of the thin chip 52, and the surface of the distal probe part 29 coming into contact with the clamping surface are coated with a ceramic in order to improve the smoothnesses of the surfaces and the mechanical strengths thereof. Areas of the surfaces which are polished or coated with a ceramic may be at least contact areas of the surfaces of the distal probe part 29 and thin chip 52.

Next, the operation of the ultrasonic incision/coagulation appliance 1 of this embodiment will be described.

The description will proceed on the assumption that the ultrasonic incision/coagulation appliance is used to treat the inside of the abdominal cavity under endoscopic viewing.

First, the sheath 2 of the ultrasonic incision/coagulation appliance 1 constructed as shown in FIG. 1 is guided to a region to be treated inside the abdominal cavity by utilizing, for example, a trocar and cannula. The movable operation handle 12 of the ultrasonic incision/coagulation appliance 1 is parted from the stationary handle 11. This causes the jaw 41 to open relative to the distal probe part 29. A tissue to be clamped is positioned in an open space between the jaw 41 and distal probe part 29.

Thereafter, the movable operation handle 12 is turned toward the stationary handle 11. This causes the jaw 41 to close gradually so as to move toward the distal probe part 29. Consequently, the living tissue is clamped by the distal probe part 29 and jaw 41.

In this state, the ultrasonic transducer drive power source is actuated in order to drive the ultrasonic transducer within the handpiece, whereby ultrasonic waves are generated. Ultrasonic vibrations generated by the ultrasonic transducer are propagated to the distal probe part 29 via the horn 24 and probe 25. The ultrasonic vibrations propagated to the distal probe part 29 cause the distal probe part 29 to vibrate. The vibrations are propagated from the distal probe part 29 to the clamped living tissue. The living tissue is then incised and coagulated due to frictional heat.

At this time, it is continued to apply ultrasonic vibrations to the living tissue. Besides, the quantity of clamping force exerted to clamp the living tissue is increased by further turning the movable operation handle 12 toward the stationary handle 11. This causes the jaw 41 to approach the distal probe part 29. Thus, coagulation proceeds while the living tissue is being incised. Consequently, incision of the living tissue is completed without bleeding.

Thereafter, the treatment assembly 26 is moved to a new treatment region while the abdominal cavity is looked through an endoscope. At this time, the positional relationship between the hand-held operation unit and treatment assembly 26 is not always the same as the relationship attained during the previous treatment. In other words, a living tissue that is an object of clamping is not always traversing a direction in which the jaw 41 opens or closes to clamp a living tissue most easily. In this case, the rotation knob 17 is manipulated in order to rotate the sheath 2 by a desired magnitude. This causes the distal spacer 32 located extremely distally within the sheath and coupled with the sheath 2 with the rotation thereof disabled to rotate.

When the distal spacer 32 rotates, the clamping member unit 22 including the operation rod 34 inserted in the distal spacer 32 as well as the other spacers 31, and the ultrasonic transducer unit 21 including the probe 25 rotate in unison. In other words, the sheath 2 rotates about the axis thereof in unison with the treatment unit 5 composed of the ultrasonic transducer unit 21 and clamping member unit 22.

This causes the direction of open or close for clamping of the jaw 41 relative to the distal probe part 29 to change. Consequently, the distal probe part 29 and jaw 41 are oriented so that they can clamp a living tissue most easily. Thereafter, as mentioned above, a living tissue is positioned to establish the positional relationship that the living tissue that is an object of clamping will traverse a direction in which the jaw 41 opens or closes, and then treated.

In this embodiment, assuming that a living tissue is clamped by the distal probe part 29 and jaw 41 which are made of a metallic material and then incised at an ultrasonic frequency, when cutting the living tissue is completed, the surface of the distal probe part 29 and the thin chip 52 included in the jaw 41 abut on each other. At this time, since the distal probe part 29 does not abut directly on the jaw body 40 but abuts on the thin chip 52 put in the clamping ditch 51, occurrence of a violent and loud mechanical sound due to the direct abutment of the distal probe part 29 on the jaw body 40 made of a metallic material can be suppressed.

The jaw 41 that is a clamping member is not made of a resin material such as so-called Teflon. It can be prevented that the clamping member is damaged, such as, deformed, melted to be burnt, or worn out because of heat stemming from ultrasonic vibrations generated during ultrasonic treatment and clamping force. This results in the greatly improved thermal and mechanical durabilities of the jaw 41 that is the clamping member compared with those of a resin clamping member. Ultrasonic treatment can be conducted with high power, and treatment efficiency can be improved.

In this embodiment, the distal probe part 29 serving as a stationary cutter that is a constituent part of the ultrasonic treatment assembly 26 is formed as an integral part of the probe 25. Talking of using a titanium material to produce the probe 25, since the titanium material is resistive to destructive distortion, has breaking strength, and is well acceptable to a living body, it is an optimal material. However, the titanium material is hard to machine and expensive. By contrast, assuming that an aluminum material is used to produce the probe 25, the aluminum material has relatively good machinability and is inexpensive. However, there is a problem in strength that the aluminum material is susceptible to heat stemming from vibrations. When the probe 25 is designed to be expendable, it may be made of an aluminum material. When emphasis is put on treatment such as incision or coagulation, at least the distal probe part 61 should preferably be made of a titanium material.

Figure 10A:
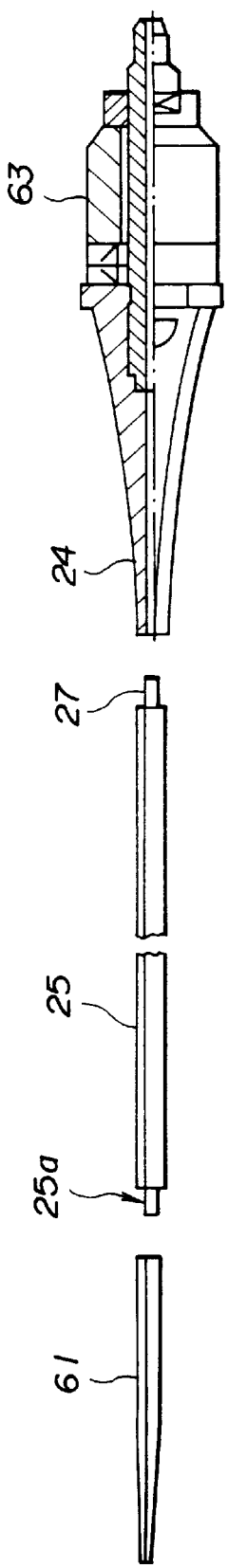
FIGS. 10A to 10C are diagrams showing an example of the structure of a probe.
Figure 10B:
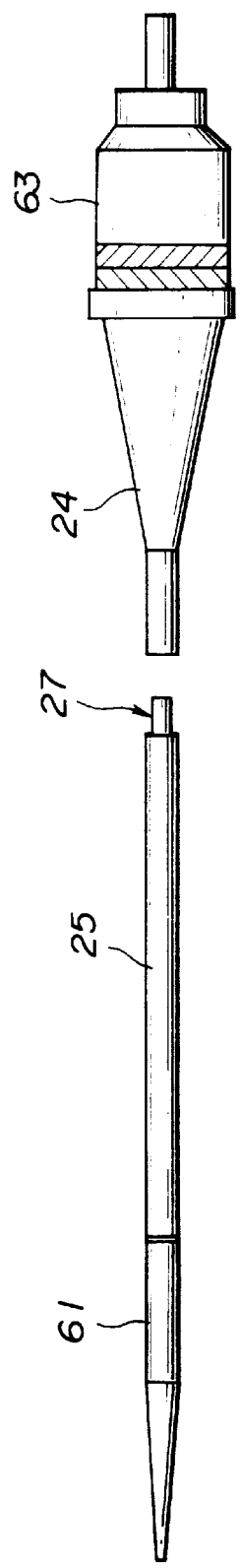

It is therefore recommended that the distal probe part 61 is, as shown in FIGS. 10A and 10B, formed with a member independent of the probe 25. Specifically, as shown in FIGS. 10A and 10B, the distal probe part 61 is made of a titanium material characterized by high durability, while the probe 25 serving as a vibration propagation member is made of an inexpensive aluminum material. The distal probe part 61 is designed to be freely attachable to or detachable from the distal end of the probe 25.

Figure 10C:
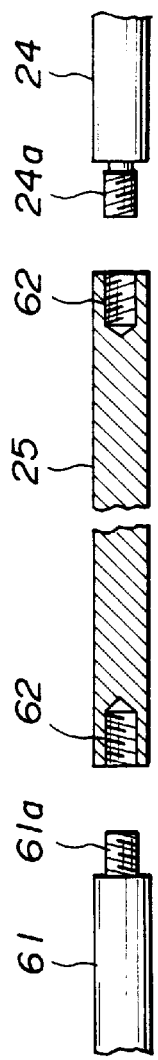

As shown in FIG. 10A, the distal probe part 61 is freely attachable or detachable via a male screw 25a formed on the distal side of the probe 25. The horn 24 is freely attachable or detachable via a male screw 27 formed on the proximal side of the probe 25. Instead of forming the male screws 25a and 27 on both sides of the probe 25 as shown in FIGS. 10A and 10B, as shown in FIG. 10C, male screws 61a and 24a may be formed on the distal probe part 61 and horn 24 respectively, and female threads 62 may be formed at both ends of the probe 25. In this case, the male screws 61a and 24a are engaged with the female screws 62. Thus, the distal probe part 61 can be freely detachably attached to the probe 25 by screwing the distal probe part 61 to the distal end of the probe 25. The probe 25 can be freely detachably attached to the horn 24 by screwing the back end of the probe 25 to the horn 24.

The distal probe part 61 that is a constituent part of the ultrasonic treatment assembly 26 and the horn 24 for supplying ultrasonic vibrations generated by the ultrasonic transducer 63 to the probe 25 are made of a high-durability titanium material, and the probe 25 serving as a relay member for linking the horn 24 and distal probe part 61 is made of an inexpensive aluminum material. Thereby, the inexpensive ultrasonic incision/coagulation appliance can be provided without deterioration of treatment performance such as performance of incision or coagulation.

Figure 11:
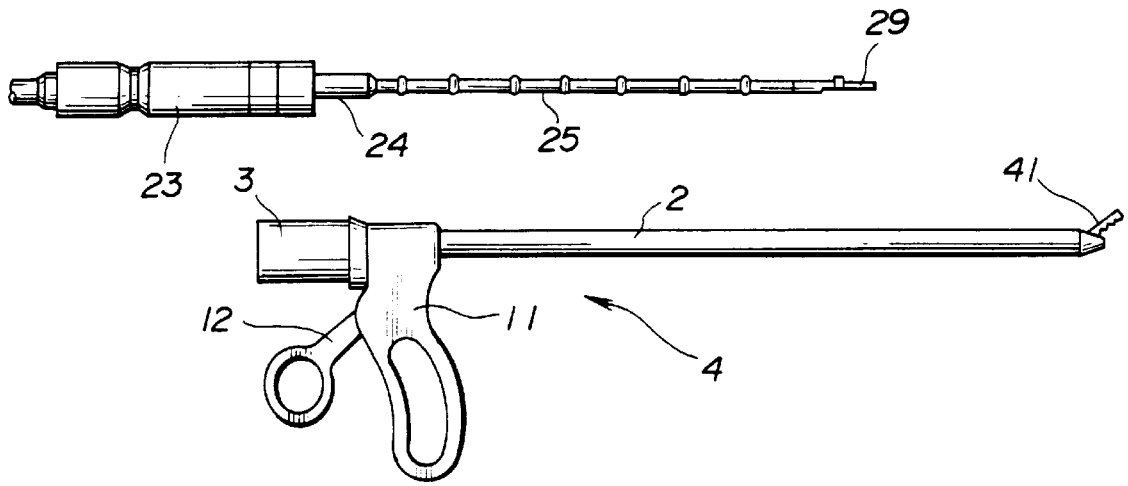
FIG. 11 is a view showing an ultrasonic incision/coagulation appliance having a jaw on a sheath thereof.

The jaw 41 serving as a clamping member is not limited to the structure in which the jaw is attached to the distal spacer 32 so that the jaw can pivot freely. Alternatively, as shown in FIG. 11, the jaw may be attached to the distal end of the sheath 2 so that the jaw can pivot freely.

Figure 12:
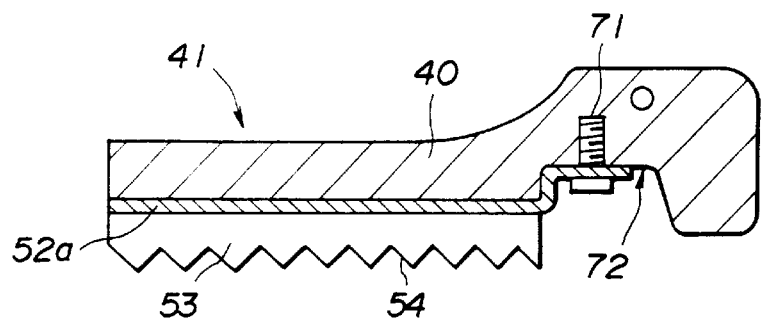
FIG. 12 is a diagram showing a structure in which a thin chip is attached to a jaw body in accordance with the second embodiment of the present invention.

Referring to FIG. 12, the second embodiment of the present invention will be described.

In this embodiment, the structure in which a thin chip is attached to a jaw body is different from that in the first embodiment. The other components of this embodiment and the operation thereof are identical to those of the first embodiment. The same reference numerals are assigned to the same members. The description of the members will be omitted.

As illustrated, a metallic thin chip 52a is affixed to the bottom of the clamping ditch 51 formed in the jaw body 40, and the proximal portion of the thin chip 52 is fixed to the jaw body 40 using a screw 71. For preventing the head of the screw 71 from jutting toward the clamping side of the jaw body, the proximal portion of the clamping ditch 51 of the jaw body 40 is formed as a recess 72 that is deeper than the thickness of the head of the screw 71. The proximal portion of the thin chip 52 is screwed in this recess 72.

Figure 13:
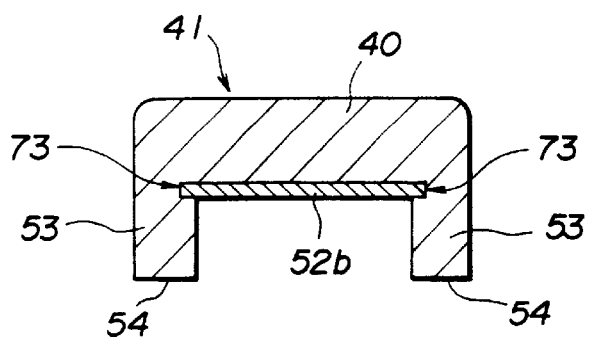
FIG. 13 is a diagram showing another structure in which a thin chip is attached to a jaw body in accordance with the third embodiment of the present invention.

Since the thin chip 52 is fixed to the jaw body 40 as an integral part of the jaw body using an adhesive and the screw 71, the attached state of the thin chip 52 to the jaw body 40 can be made more reliable. Compared with the work of fixing the thin chip 52 to the jaw body 40 using an adhesive alone, workability improves markedly. Referring to FIG. 13, the third embodiment of the present invention will be described.

In this embodiment, the structure in which a thin chip is attached to a jaw body is different from those in the first and second embodiments. The other components of this embodiment and the operation thereof are identical to those of the aforesaid embodiments. The same reference numerals are assigned to the same members. The description of the members will be omitted.

As illustrated, fitting grooves 73 to which the side margins of a thin chip 52b are fitted and fixed are bored on both right-hand and left-hand sides of the bottom of the clamping ditch 51 formed in the jaw body 40. In other words, the width of the thin chip 52b is made larger than the width of the ditch. The side margins of the thin chip 52b are fitted into the fitting grooves 73, whereby the thin chip 52b is attached to the jaw body 40 in order to construct the jaw 41.

Since the thin chip 52b is thus fixed to the jaw body 40 by fitting the thin chip 52b into the fitting grooves 73, the necessity of an adhesive or screw is obviated. Consequently, the time-consuming fixing work of snap fitting, spot welding, or laser point welding becomes unnecessary.

Figure 14:
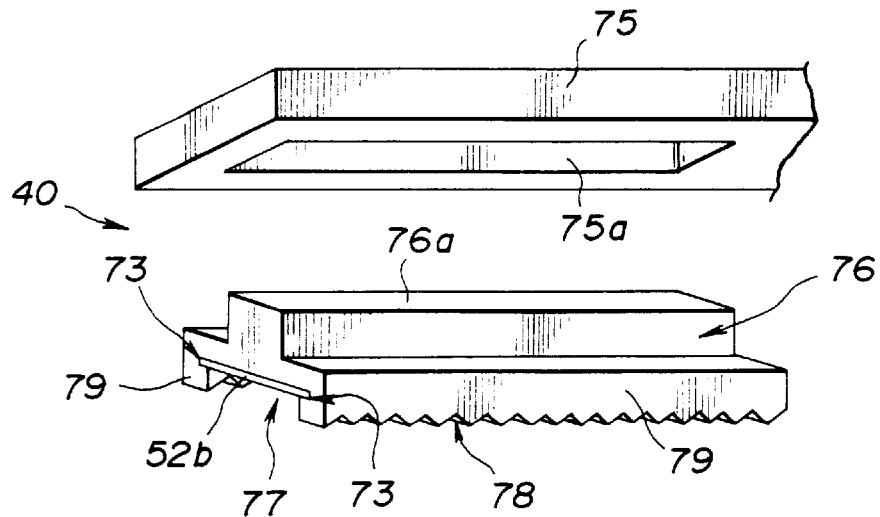
FIG. 14 is a view showing another structure of a jaw in accordance with the fourth embodiment of the present invention.

Referring to FIG. 14, the fourth embodiment of the present invention will be described.

In this embodiment, the structure of a jaw body is different from those in the first, second, and third embodiments.

To be more specific, as illustrated, the jaw body 40 in this embodiment has a metallic supporting portion 75, which is attached to the distal spacer 32 so that the supporting portion 75 can pivot freely, independently of a clamping portion 76 including a clamping ditch 77 that provides a clamping surface in a longitudinal direction, and jutting rims 79 jutting out from both margins of the clamping ditch 77 and having a plurality of triangular teeth 78 on the clamping sides of the jutting rims. The clamping portion 76 is freely attachable to or detachable from the supporting portion 75.

The supporting portion 75 has an attachment hole 75a enabling the clamping portion 76 to be freely attached to or detached from the supporting portion 75. On the other hand, the clamping portion 76 has an engagement convex part 76a that is freely removably fitted into the attachment hole 75a.

At least the engagement convex part 76a of the clamping portion 76 is made of a material having elasticity. The clamping portion 76 is fixed to the supporting portion 75 in one united body by press-fitting the engagement convex part 76a into the attachment hole 75a.

The thin chip 52 made of stainless steel or a ceramic material and serving as an auxiliary member is fitted into the fitting grooves 73 in the clamping ditch 77 of the clamping portion 76. The other components of this embodiment and the operation thereof are identical to those of the aforesaid embodiments. The same reference numerals are assigned to the same members. The description of the members will be omitted.

Since the clamping portion 76 is designed to be freely attachable to or detachable from the supporting portion 75, the clamping portion 76 can be replaced with a new one readily. For example, when the triangular teeth 78 formed on the clamping side of the clamping portion are worn down, the clamping portion 76 can be replaced with another clamping portion prepared in advance. Thus, a desired quantity of clamping force can be restored.

As mentioned above, a resin material such as Teflon is readily damaged by heat stemming from ultrasonic vibrations or clamping force. However, since the clamping portion 76 can be replaced with a new one readily, when at least the triangular teeth 78 of the clamping portion 76 are made of a resin material, it can be prevented that a living tissue burns and sticks to the teeth 78 during treatment.

Furthermore, when the whole clamping portion 76 is made of a resin material such as Teflon and the thin chip 52b is put in the clamping ditch 77, even if the distal probe part 29 abuts directly on the resin clamping portion 76, it can be prevented that the clamping portion 76 made of a resin material is melt down by heat stemming from ultrasonic vibrations. Besides, occurrence of a loud mechanical sound can be prevented.

Figure 15:
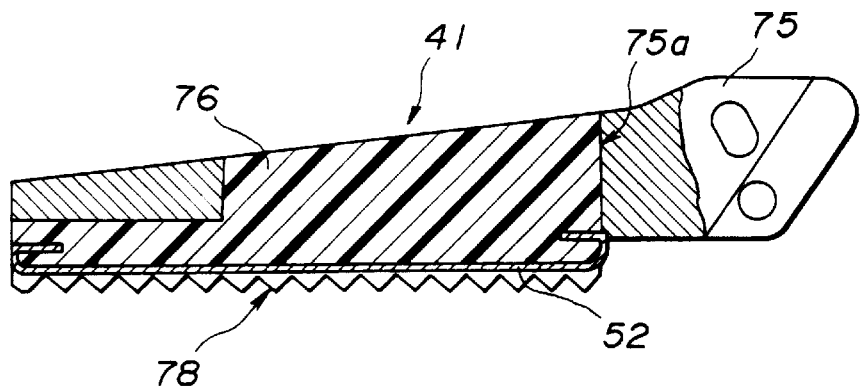
FIG. 15 is a diagram showing a state in which a clamping portion provided with a thin chip through insert molding is mounted in a supporting portion.
Figure 16:
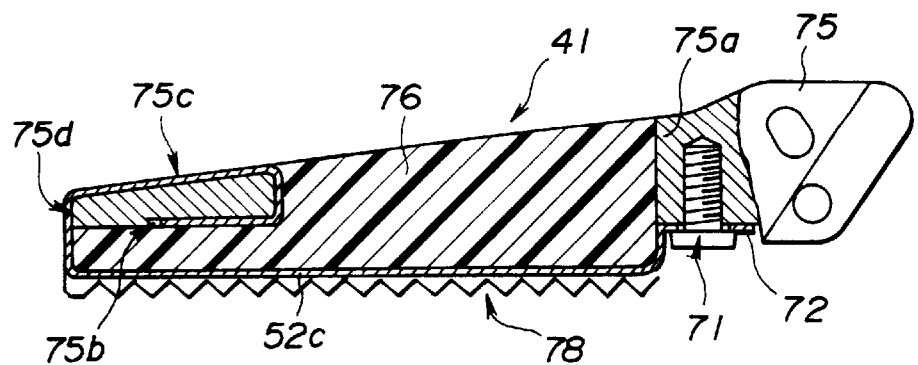
FIG. 16 is a diagram showing a state in which a thin chip and clamping portion are attached to a supporting portion.

In the process of producing the clamping portion 76 freely attachable to or detachable from the supporting portion 75 using a heat resisting resin material such as Teflon, the thin chip 52 may be, as shown in FIG. 15, formed as an integral part of the clamping portion 76 by performing molding. Otherwise, as shown in FIG. 16, one end of a thin chip 52c may be put in a concave part 75b of the lower surface of the supporting portion 75. The thin chip 52c may then be routed through a distal end surface of the attachment hole 75a, laid on the upper surface 75c and distal end surface 75d of the supporting portion 75, and finally led to the clamping ditch 77. The other end of the thin chip 52c may be fixed to the supporting portion 75 using the screw 71.

Figure 17:
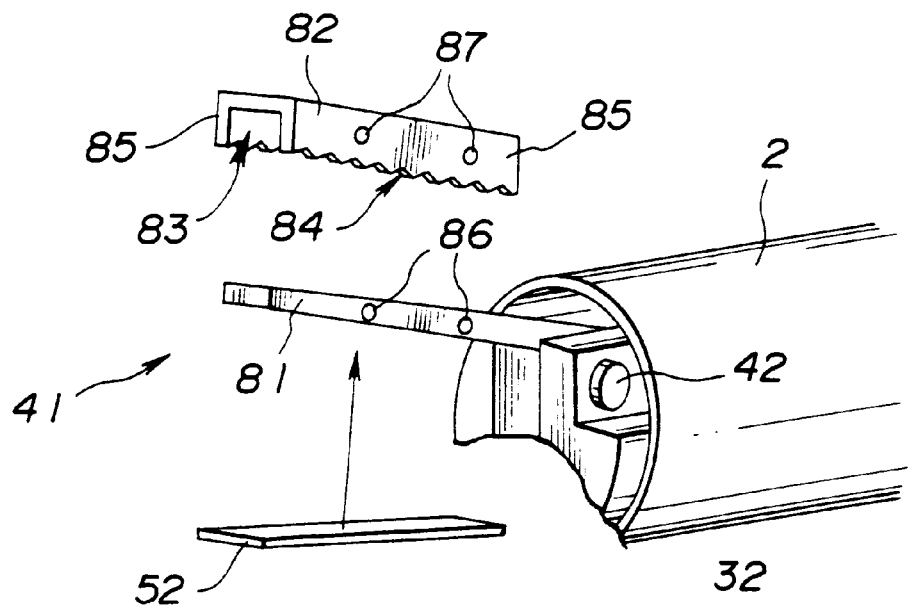
FIGS. 17 and 18 are views for explaining the fifth embodiment of the present invention.
Figure 18:
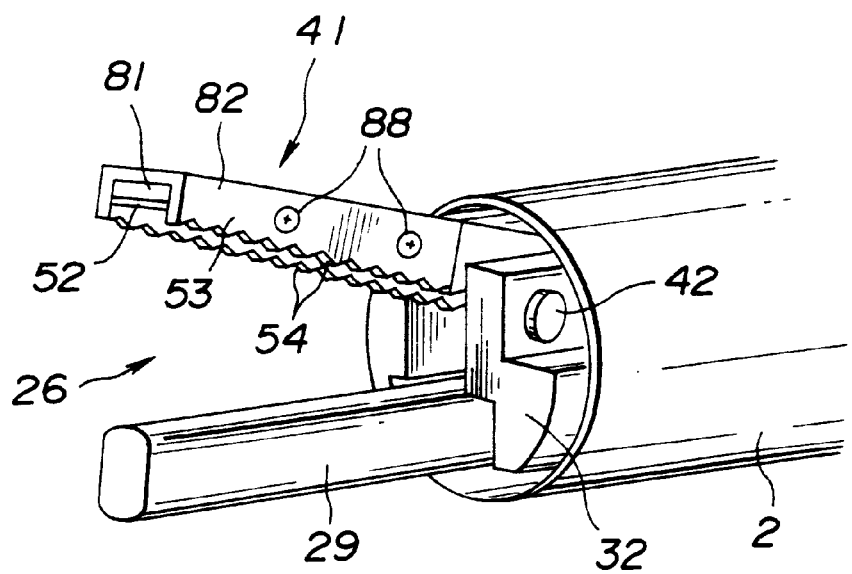

Referring to FIGS. 17 and 18, the fifth embodiment of the present invention will be described.

A jaw in this embodiment is composed of a supporting portion and clamping portion like the jaw in the fourth embodiment, but has a different structure.

As shown in FIG. 17, the jaw 41 is composed of a movable cutter body 81 made of a metal and also serving as a plate-like supporting portion, and a cover 82 made of a heat resisting resin material such as Teflon and covered over the movable cutter body 81. The thin chip 52 is affixed to the lower surface of the movable cutter body 81 using an adhesive.

The cover 82 has, as mentioned above, a clamping ditch 83, jutting rims 85 jutting out from both edges of the clamping ditch 83 and having triangular teeth 84 on the clamping sides of the jutting rims, and through holes 87 bored coincidentally with screw holes 86 formed in the movable cutter body 81 so that screws can be inserted into the through holes 87.

In short, as shown in FIG. 18, the cover 82 is fixed to the movable cutter body 81 using screws 88. Owing to this structure, the same operation and advantage as those of the fourth embodiment can be exerted.

In this embodiment, the cover 82 is fixed to the movable cutter body 81 using the screws 88. Instead of forming the screw holes 86 in the movable cutter body 81, dummy holes may be formed, the cover 82 may be joined with the movable cutter body 81 using pins that are not shown, and then the joints may be caulked. For attaching the cover 82 to the movable cutter body 81, the movable cutter body 81 may be provided with a convex part and the cover 82 may be provided with a through hole into which the convex part is fitted.

Figure 19:
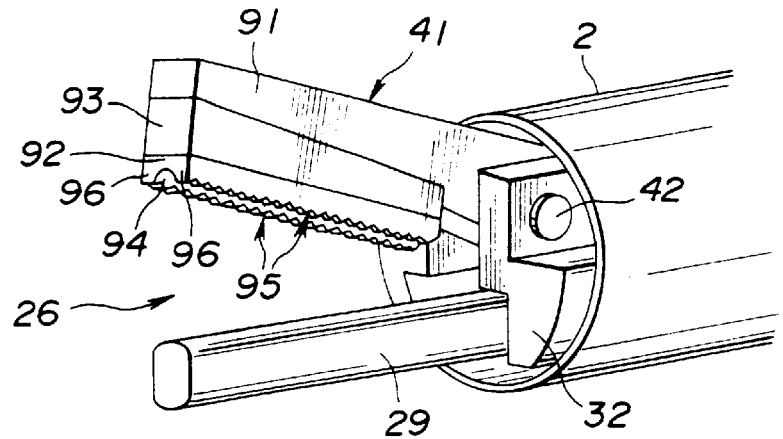
FIGS. 19 and 20 are views for explaining the sixth embodiment of the present invention.
Figure 20:
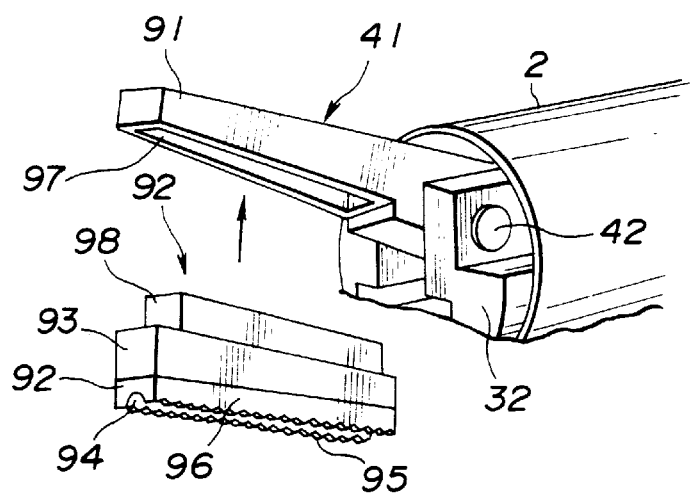

Referring to FIGS. 19 and 20, the sixth embodiment of the present invention will be described.

A jaw in this embodiment is composed of a supporting portion and clamping portion like the jaws in the fourth and fifth embodiments. However, an elastic member serving as an auxiliary member for providing a sufficient quantity of clamping force is interposed between the supporting portion and clamping portion.

As shown in FIG. 19, the jaw 41 is composed of a supporting portion 91, clamping portion 92, and a linkage rubber 93 serving as an auxiliary member made of a rubber material which is an elastic member interposed between the supporting portion 91 and clamping portion 92. The linkage rubber 93 and clamping portion 92 are formed by, for example, performing insert molding or assembled in one united body using an adhesive. A clamping ditch 94 and jutting rims 96 having triangular teeth 95 are formed on the clamping side of the clamping portion 92.

As shown in FIG. 20, an attachment hole 97 making it possible to freely attach or detach the clamping portion 92 and linkage rubber 93 which are assembled in one united body is bored in the lower surface of the supporting portion 91 on the treatment side of the supporting portion. A fitting convex part 98 to be fitted into the attachment hole 97 in the supporting portion 91 is formed on the upper surface of the linkage rubber 93.

The fitting convex part 98 formed on the linkage rubber 93 is press-fitted into the attachment hole 97 bored in the supporting portion 91 as indicated with an arrow in FIG. 20. The linkage rubber 93 is then, as shown in FIG. 19, linked with and fixed to the supporting portion 91 in one united body. The supporting portion 91 may be provided with a setscrew or projection for preventing the linkage rubber 93 from coming off, or the linkage rubber 93 may be fixed to the supporting portion 91 using a fixing means such as an adhesive.

As mentioned above, the linkage rubber 93 is interposed between the supporting portion 91 and clamping portion 92 constituting the jaw 41. Consequently, when a living tissue is clamped by the distal probe part 29 and jaw 41, since the linkage rubber 93 of the jaw 41 deforms elastically in line with deflection of the probe 25 so as to absorb deflection of the distal probe part 29, the living tissue can be clamped reliably. When a living tissue is clamped by the distal probe part 29 and jaw 41, stronger force can be exerted. The living tissue will therefore not come off. This leads to improvement of a treatment ability.

Moreover, since the clamping portion 92 of the jaw 41 is brought into contact with the living tissue, it can be prevented that an elastic member such as the linkage rubber 93 is brought into direct contact with a living tissue. It can therefore be prevented that the elastic member such as the linkage rubber 93 comes into direct contact with a living tissue and is melt by heat stemming from ultrasonic vibrations generated during ultrasonic treatment. A living tissue can therefore be treated efficiently using high-power ultrasonic vibrations without the need of restricting an ultrasonic output during ultrasonic treatment.

Incidentally, the clamping portion 92 may be made of either a metallic material or a resin material such as Teflon. In this case, the thin chip 52 described in relation to the first to fifth embodiments is designed in conformity with the clamping portion made of either of the materials. This results in an ultrasonic treatment appliance in which occurrence of a noise is minimized, deterioration of an incision/coagulation ability caused by heat is prevented, and a sufficient quantity of clamping force is available.

Figure 21:
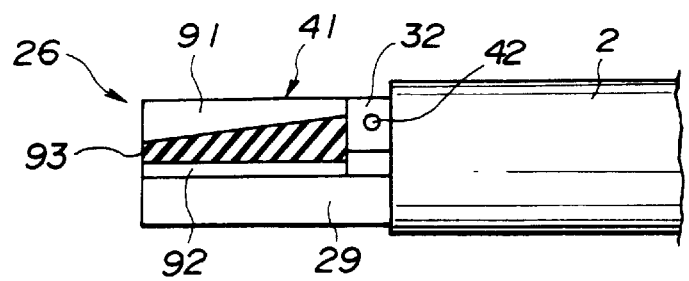
FIG. 21 is a diagram showing a jaw that includes an elastic member and has another structure in accordance with the seventh embodiment of the present invention.

Referring to FIG. 21, the seventh embodiment of the present invention will be described.

As illustrated, in this embodiment, the thickness of the distal portion of the linkage rubber 93 that is a constituent part of the jaw 41 in the sixth embodiment is tapered relative to the thickness of the back end thereof.

In this embodiment, therefore, if the magnitude of deflection of the distal probe part 29 changes in relation to a position in an axial-center direction, the thickness of the linkage rubber 93 is changed according to the property of the distal probe part 29 on the magnitude of deflection. Thus, the deflection of the distal probe part 29 can be absorbed more effectively.

Figure 22:
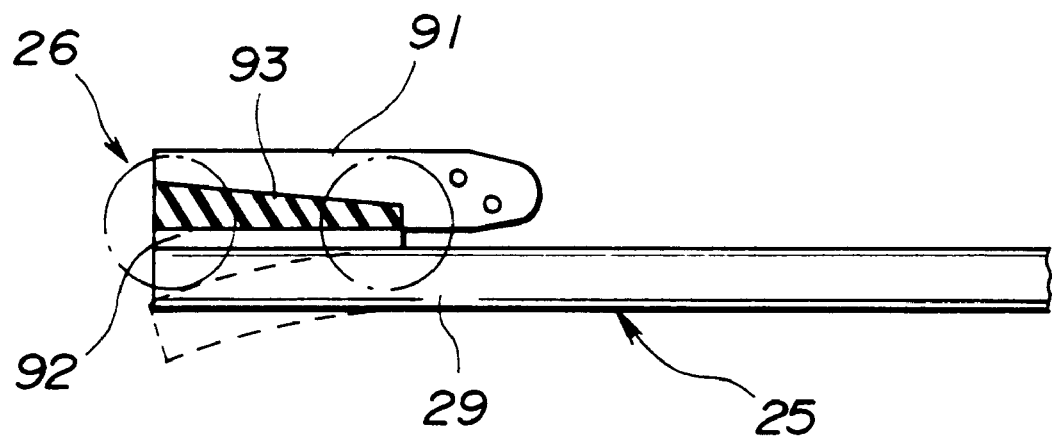
FIG. 22 is a diagram for explaining the operation of a jaw including an elastic member and having another structure.

When the linkage rubber 93 is, as shown in FIG. 22, designed so that the thickness of the distal portion thereof gets gradually larger relative to the thickness of the back end thereof, if the magnitude of deflection of the distal portion of the distal probe part 29 is larger than that of the proximal portion thereof, the deflection of the distal probe part 29 can be absorbed efficiently. The linkage rubber 93 may be designed so that the thickness thereof changes intermittently in an axial-center direction.

Figure 23:
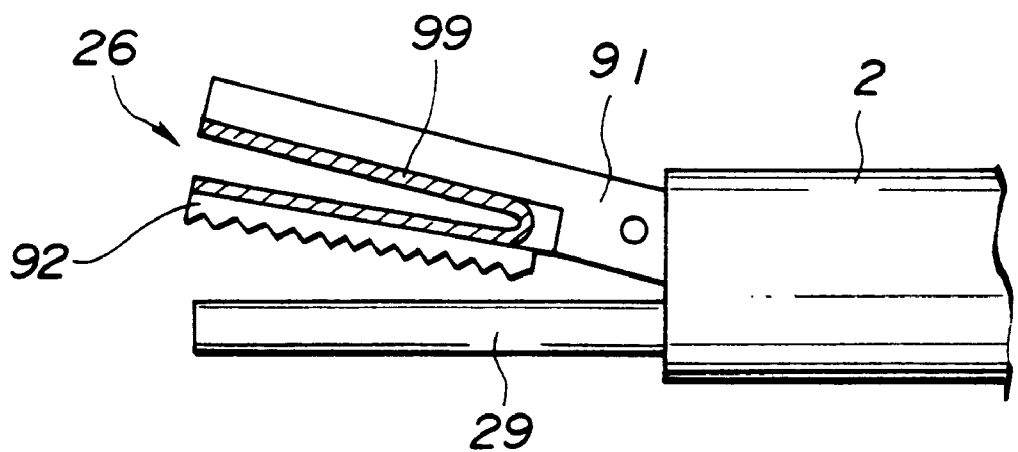
FIG. 23 is a diagram showing a jaw constructed by interposing a spring as an elastic member between a clamping portion and supporting portion.

Moreover, as shown in FIG. 23, a blade spring 99 shaped substantially like letter U may be placed instead of interposing the linkage rubber 93 between the supporting portion 91 and clamping portion 92 of the jaw 41. The same operation and advantage as those of the sixth embodiment can still be exerted.

Figure 24:
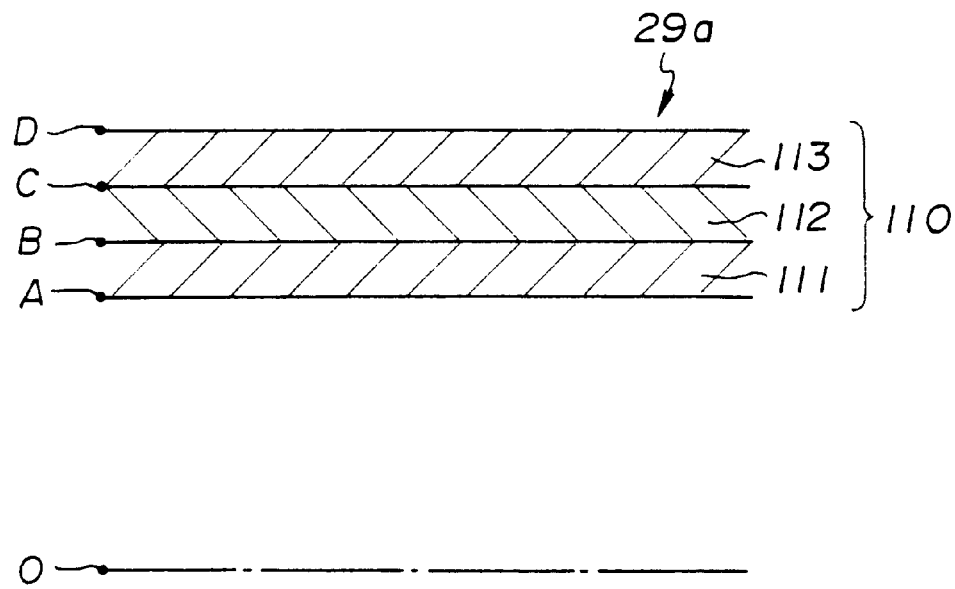
FIGS. 24 and 25 are diagrams for explaining the eighth embodiment of the present invention.
Figure 25:
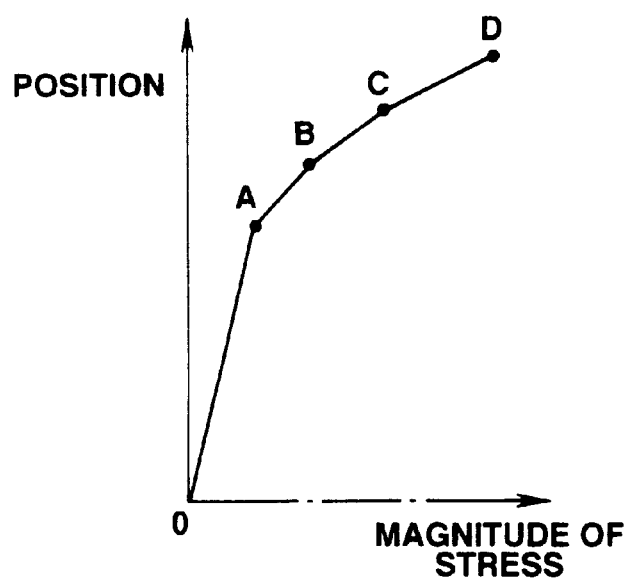

Referring to FIGS. 24 and 25, the eighth embodiment will be described below.

As shown in FIG. 24, three coating layers 111, 112, and 113 having a thickness of 3 $\mu$m are laid over the outer circumference of a distal probe part 29a orderly from the center O of the distal probe part indicated with a dot-dash line. A solid line A in the drawing indicates an interface between a base material and the coating layer 111. A solid line B indicates an interface between the coating layer 111 and coating layer 112. A solid line C indicates an interface between the coating layer 112 and coating layer 113. A solid line D indicates the surface of the outer coating layer. Incidentally, the base material is a titanium alloy.

A coating surface 110 composed of the three layers of the coating layers 111, 112, and 113 covers a portion of the distal probe part 29a that may rub against another member at least in the longitudinal direction of the distal probe part 29a and may then abrade. The coating surface 110 also covers a portion of the distal probe part 29a that juts out of the clamping member sheath 3 and is exposed to outside.

Incidentally, the coating surface 110 may be formed to cover nodes of ultrasonic vibrations or formed over the whole length of the distal probe part 29a.

Moreover, a magnitude of abrasion occurring when the distal probe part 29a meets the jaw 41 normally ranges from about 5 $\mu$m to 6 $\mu$m. The thickness of the coating surface 110 is solely approximately 3 $\mu$m. When the coating surface 110 is solely formed on the distal probe part 29a, the base material is exposed readily due to abrasion. For the distal probe part 29a, therefore, the coating surface 110 must have a thickness of at least 6 $\mu$m. Experimentally, the most preferable structure of a coating surface is realized by laying the coating surface 110 three times or more so that the total thickness of coating films will be 8 $\mu$m or more.

The plurality of coating layers 111, 112, and 113 is overlaid on the base material as mentioned above. Consequently, a stress gradient expressed by adjoining ones of points plotting a curve shown in FIG. 25, which indicate stresses distributed to positions O, A, B, C, and D on the distal probe part 29a, gets smaller. This means that occurrence of a crack due to stresses induced among the layers can be suppressed.

For example, as long as practical requirements including cost are ignored, it is feasible to deposit a sole coating layer having a thickness of 6 $\mu$m or more according to the PVD. By the way, an experiment was conducted. Namely, one probe was coated with a coating layer having a thickness of 9 $\mu$m. By contrast, another probe was coated with a plurality of coating layers like the one employed in the present invention, that is, three coating layers, each of which has a thickness of 3 $\mu$m, of 9 $\mu$m in total thickness. These probes having the same thickness were vibrated ultrasonically. The experiment has demonstrated that the probe coated with the sole coating layer had the coating layer peeled off from a base material more readily than the probe coated with the plurality of coating layers.

The foregoing fact is apparent from FIG. 25. Namely, the coating surface constructed by placing the plurality of coating layer can suppress occurrence of a crack, which stems from stresses induced in the layers, more effectively than the coating surface constructed with the sole layer.

Moreover, the experiment has demonstrated that even a probe coated with a coating layer having a thickness of 10 $\mu$m or more is readily cracked. This is attributable to a relationship between the coating layer itself and a base material, that is, a stress gradient observed between them.

Next, the operations of the distal probe part 29a having the coating surface composed of three coating layers will be described particularly.

First, the distal probe part 29a of the handpiece 1 is abutted on a desired region of a patient to be treated. Thereafter, the handle 12 is manipulated in order to catch a tissue, to which ultrasonic vibrations should be applied, between the distal probe part and jaw 41. In response to an input from a switching means that is not shown, the ultrasonic transducer starts vibrating. The ultrasonic vibrations are propagated to the distal probe part 29a.

Owing to the action of frictional heat stemming from the ultrasonic vibrations, any desired treatment such as coagulation or incision is performed on the patient's tissue. At this time, since the distal probe part 29a is coated with a coating having sufficient abrasion resistivity and strength, a possibility that a crack may occur due to concentration of stresses deriving from abrasion is markedly low. A fear that the probe may be broken during a surgical procedure is minimized. Consequently, the efficiency and safety of the surgical procedure improves drastically.

As mentioned above, since the coating surface composed of three coating layers is formed on the surface of the distal probe part, practical requirements such as cost for application of coating layers can be satisfied. Moreover, the distal probe part can enjoy sufficient abrasion resistivity and strength. Thus, an ultrasonic treatment appliance helpful in conducting a surgical procedure efficiently and safely is realized.

Moreover, since the coating surface composed of three coating layers is formed on the distal probe part, the base material can be prevented from cracking due to a strong extraneous force such as an impact. Consequently, the durability of the handpiece improves and the service life of the appliance itself extends. This leads to improved cost performance.

In this embodiment, three coating layers each having a thickness of 3 $\mu$m are overlaid on the base material. The thickness of each coating layer is not limited to 3 $\mu$m. Any other thickness will do as long as the thickness permits satisfaction of the practical requirements such as cost.

Moreover, the number of layers to be overlaid on the base material is not limited to three but may be four or more. Even when two layers may be overlaid on the base material, certain advantages can be exerted.

Furthermore, according to this embodiment, a plurality of coating layers having the same thickness is overlaid on a base material. The easiness in detaching the coating layers from the base material has markedly improved compared with the easiness in detaching a sole coating layer. However, the larger the number of coating layer is, the greater a cost-related load is. A necessary minimum number of coating layers should naturally be adopted.

Figure 26:
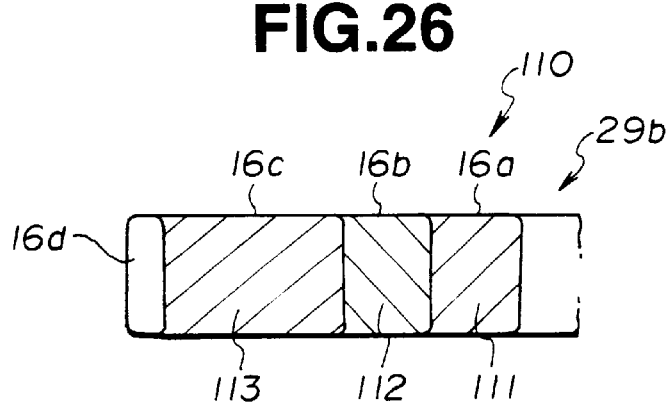
FIG. 26 is an oblique view of the distal probe part of an ultrasonic therapeutic appliance in accordance with the ninth embodiment of the present invention.

Referring to FIG. 26, the ninth embodiment of the present invention will be described below.

This embodiment is different from the eighth embodiment only in the structure of a distal probe part.

As illustrated, a distal probe part 29*b* of this embodiment has, like the one of the eighth embodiment, a coating surface 110 formed on the outer surface thereof communicating with a distal surface 116*d* thereof. The distal probe part 29*b* is characterized by areas in which the coating surface 110 is formed.

Specifically, a coating layer 111 that is a first layer is overlaid on a base material over areas 116*a*, 116*b*, and 116*c* of the distal probe part 29*b*.

Thereafter, a coating layer 112 that is a second layer is overlaid on the base material over the areas 116*b* and 116*c*. A coating layer 113 that is a third layer is then overlaid on the base material over the area 16*c* alone.

Consequently, the area 116*a* has only the coating layer 111 that is the first layer overlaid on the base material. The area 116*b* has the coating layer 111 that is the first layer and the coating layer 112 that is the second layer overlaid thereon. The area 116*c* has the three layers of the coating layer 111 that is the first layer, the coating layer 112 that is the second layer, and the coating layer 113 that is the third layer overlaid thereon.

Thus, the areas in which the coating layers are overlaid on the base material are narrowed gradually from below to upward. The operations of this embodiment are identical to those of the eighth embodiment.

As mentioned above, since the areas in which the coating layers are overlaid are narrowed gradually, a boundary between adjoining areas is defined with a line. This is because portions not to be coated are masked during coating work. Lines are therefore drawn without fail.

This is helpful in visually identifying the coating layers. Moreover, a portion untreated by the coating work can be found readily. After the entire coating work is completed, the thickness of each coating layer can be measured easily. Moreover, a coating layer having a required thickness can be formed over a portion that should be coated.

Figure 27:
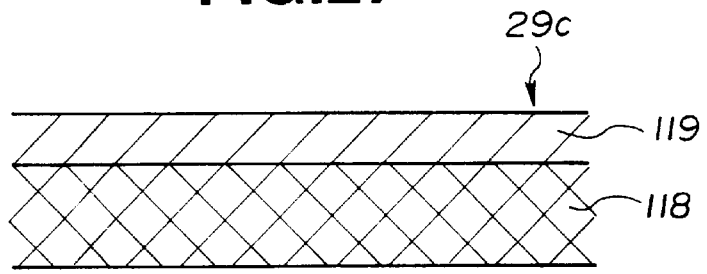
FIG. 27 is a sectional view of the distal probe part of an ultrasonic therapeutic appliance in accordance with the tenth embodiment of the present invention.

Referring to FIG. 27, the tenth embodiment of the present invention will be described below.

This embodiment is different from the eighth embodiment only in the structure of a distal probe part.

As illustrated, a coating layer 119 is formed over a distal probe part 29*c* of this embodiment according to the PVD. Moreover, an intermediate layer 118 realized with a nickel plating layer is interposed between a base material and the coating layer 119.

The Vickers hardness of the intermediate layer 118 ranges, in this embodiment, preferably, from about 800 to 1000. The other components and operations are identical to those of the eighth embodiment.

According to this embodiment, stress gradients expressed as a curve smoother than a curve expressing a stress distribution attained according to the eighth embodiment can be attained. Consequently, occurrence of a crack stemming from concentration of stresses induced in layers can be suppressed more effectively. Durability can be improved.

Figure 28:
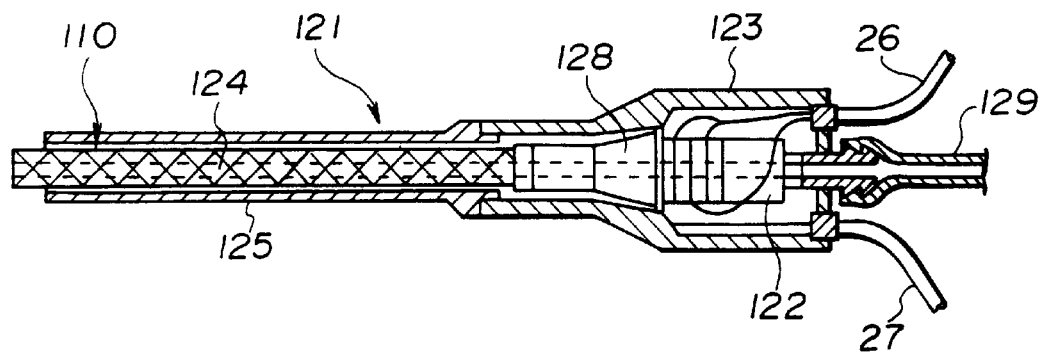
FIG. 28 is a longitudinal sectional view of a handpiece of an ultrasonic therapeutic appliance in accordance with the eleventh embodiment of the present invention.

Referring to FIG. 28, the eleventh embodiment of the present invention will be described below.

As illustrated, a handpiece 121 of this embodiment is employed in an ultrasonic suction appliance having a pipe-like probe for emulsifying a tissue by utilizing ultrasonic vibrations, sucking the resultant tissue, and thus crushing and removing a lesion.

The handpiece 121 includes a hand-held portion 123 having an ultrasonic transducer 122 incorporated therein, and a sheath 125 communicating with the hand-held portion 123 and enclosing an ultrasonic vibration propagation member 124.

A horn 128 for mechanically amplifying ultrasonic vibrations generated by the ultrasonic transducer 122 and transmitting the resultant ultrasonic vibrations to the vibration propagation member 124 is interposed between the ultrasonic transducer 122 and vibration propagation member 124. The tip of the sheath 125 is open. The pipe-like vibration propagation member 124 is jutting out of the distal side of the sheath 125.

The vibration propagation member 124 can conduct even a high-frequency current. The hollowed portion of the vibration propagation member 124 communicates with a hollow suction channel running through the horn 128 and ultrasonic transducer 122. The hollowed portion of the vibration propagation member 124 also communicates with a suction tube 129 coupled to a suction source that is not shown. A coating surface 110 similar to the one shown in FIG. 24 is formed on the circumference of the vibration propagation member 124.

Next, the operations of this embodiment will be described.

The vibration propagation member 124 of the handpiece 121 is abutted on a desired region of a patient to be treated. Thereafter, the ultrasonic transducer starts vibrating in response to an input from a switching means that is not shown. The ultrasonic vibrations are transmitted to the vibration propagation member 124.

The ultrasonic vibrations are used to emulsify a patient's tissue, suck the resultant tissue, and thus crush and remove a lesion. Moreover, when a lesion is breeding, a high-frequency current is applied to the lesion in order to cauterize the lesion.

The vibration propagation member 124 has the coating surface 110, which exhibits sufficient abrasion resistivity and strength, formed thereon. A possibility that a crack may occur due to concentration of stresses deriving from abrasion is markedly minimized. Consequently, a possibility that the probe may be broken during a surgical procedure is minimized. This leads to improved efficiency and safety of the surgical procedure.

Thus, according to this embodiment, while practical requirements for finishing such as cost are cleared, a vibration propagation member enjoying sufficient abrasion resistivity and strength can be realized. Consequently, an ultrasonic therapeutic appliance helpful in conducting a surgical procedure efficiently and safely can be realized.

Moreover, when an extraneous force oriented in a lateral direction is applied to the vibration propagation member during a therapeutic treatment, the vibration propagation member may meet the sheath. Even on such an occasion, the base material can be prevented from cracking owing to sufficient durability.

Moreover, the durability of a handpiece itself can be improved. The service life of an appliance itself can be extended. This is advantageous in terms of cost performance.

Figure 29:
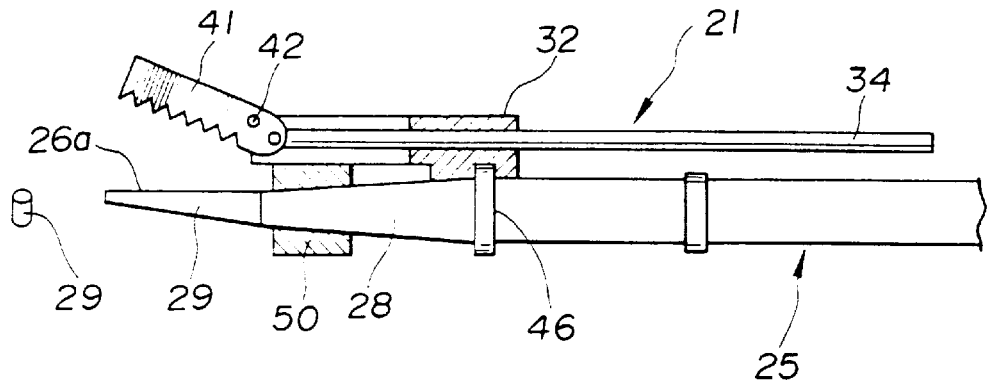
FIGS. 29 to 31 are diagrams for explaining the twelfth embodiment of the present invention.
Figure 30:
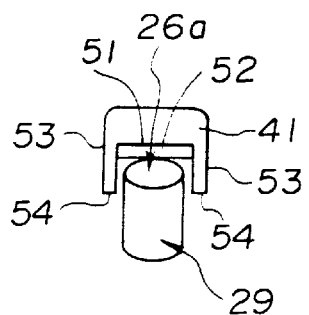
Figure 31:
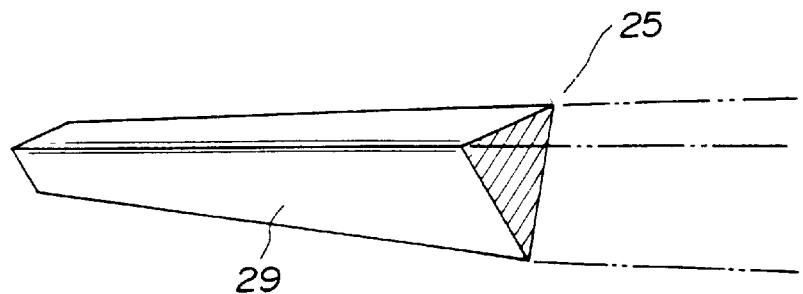

Referring to FIGS. 29 to 31, the twelfth embodiment of the present invention will be described.

As shown in FIG. 29, a jaw 41 is pivoted to a distal spacer 32, which is the leading spacer, using a pin 42. The jaw 41 is opposed to a distal probe part 29 formed as the distal part of a probe 25 so that it can cooperate with the distal probe part 29 in clamping or releasing a living tissue.

An ultrasonic treatment surface 26*a* of the distal probe part 29 that cooperates with the jaw 41 in clamping a living tissue is a flat surface. The distal probe part 29 has a longitudinal sectional shape whose area decreases gradually and continuously from the tip thereof to the root thereof. The longitudinal sectional shape is substantially rectangular. Alternatively, an inverse triangular shape shown in FIG. 31 or a semi circular shape will do.

The metallic body member of the jaw 41 is, as shown in FIG. 30, shaped to have a bracket-shaped cross section. Owing to the cross sectional shape, a clamping groove 51 is formed. A thin chip 52 that is a metallic thin plate is placed on the bottom of the clamping groove 51. The thin chip 52 placed on the bottom of the clamping groove 51 meets the blade of the distal probe part 29 (upper side thereof).

When a living tissue is clamped between the distal probe part 29 and jaw 41, a uniform load is applied to the distal part 29 of the probe 25 by the jaw 41. A bending stress induced in the distal probe part 29 increases gradually from the tip of the distal probe part to the root thereof.

Owing to the aforesaid sectional shape, the section modulus of the distal part 29 of the probe 25 increases gradually from the tip thereof to the root thereof similarly to the bending stress. The stress induced in the distal probe part 29 is therefore suppressed. In this case, the probe 25 should preferably be structured not to warp.

Assume that the probe 25 or especially the distal part 29 thereof will not warp. When the probe 25 that is vibrating ultrasonically and the jaw 41 clamp a living tissue to coagulate or cut away the tissue using frictional heat, the whole clamping portions of the probe and jaw can be employed. Consequently, the coagulation or cutting can be achieved on a stable basis. Thus, any treatment can be achieved safely.

Moreover, even when a small crack or the like is created on the upper side of the probe 25, an excess bending stress will not be induced in the probe 25. A load stress causing a fatigue crack will therefore not be induced. The probe 25 will therefore not be broken. Consequently, the durability and strength of the probe 25 can be improved drastically.

Moreover, the sectional shape of the distal part 29 of the probe 25 may, as shown in FIG. 31, be an inverse triangle. In this case, two lower sides of the triangle define a sharp angle. This means that a field of view permitted at the distal end of a clamping member can be seen fully. Consequently, the efficiency in treating a tissue improves.

Figure 32:
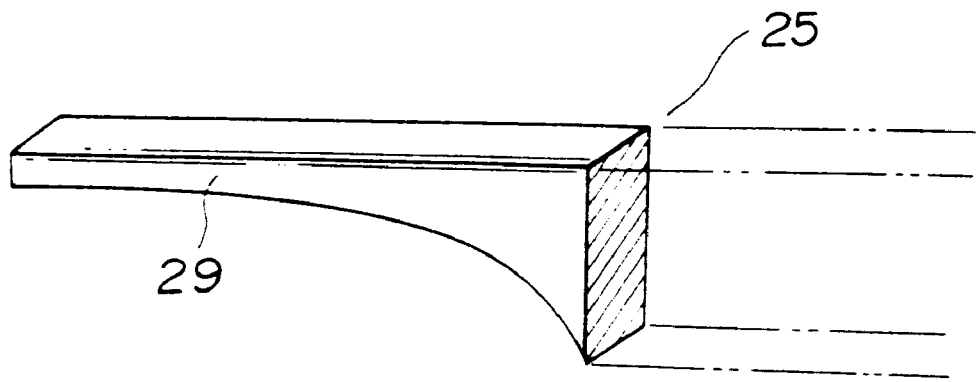
FIG. 32 is a longitudinal sectional view showing another structure of a clamping member of an ultrasonic incision/coagulation.

Alternatively, the longitudinal sectional shape of the distal part 29 of the probe 25 may be, as shown in FIG. 32, a streamlined shape drawing a curve that descends from the tip thereof to the root thereof, or preferably, an exponential curve. Otherwise, a longitudinal sectional shape whose area increases as an exponential function will do.

A theoretical bending stress induced when a uniform load is applied to the probe 25 is plotted as an exponential curve relative to a position on the distal probe part. The position shifts in a direction, in which a load is applied, from a distal position on the distal probe part to a proximal position thereon. An increase in section modulus induced in the distal probe part 29 corresponds to a stress distribution in the distal probe part. From this viewpoint, this embodiment is preferable to the aforesaid embodiments. Moreover, since the bending stress induced in the probe 25 can be suppressed strictly, a risk of a fatigue failure can be suppressed more successfully.

Figure 33:
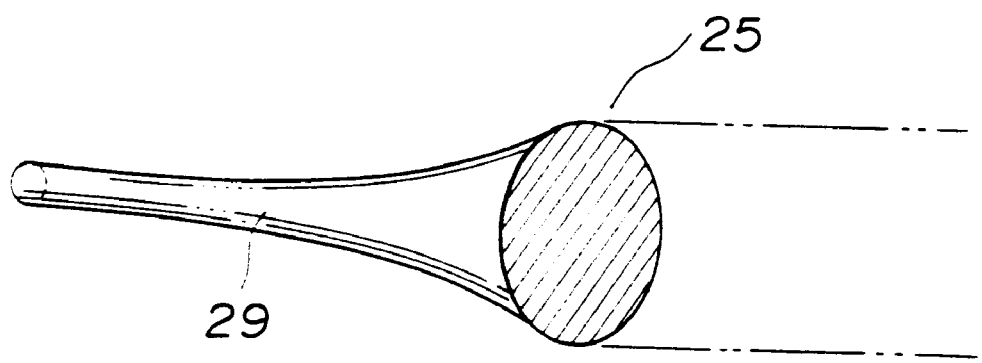
FIG. 33 is a longitudinal sectional view showing another structure of a clamping member of an ultrasonic incision/coagulation appliance.

Moreover, the cross sectional shape of the distal part 29 of the probe 25 may be, as shown in FIG. 33, a circle that gets larger from the tip of the distal part to the root thereof. The sectional area increases gradually, or preferably, increases as an exponential function relative to a position on the distal part.

A theoretical bending stress induced when a uniform load is applied to the probe 25 is plotted as an exponential curve relative to a position on the distal probe part. The position shifts in a direction, in which the load is applied, from a distal position on the distal probe part to a proximal position thereon. An increase in section modulus of the distal probe part 29 corresponds to a stress distribution in the distal probe part. From this viewpoint, this embodiment is preferable to the aforesaid embodiments. Moreover, since the bending stress induced in the probe 25 can be suppressed strictly, a risk of a fatigue failure can be suppressed more successfully.

In the present invention, it will be apparent that a wide range of different embodiments can be constituted on the basis of the invention without a departure from the spirit and scope of the invention. This invention is limited to the accompanying claims but not restricted to any specific embodiment.

What is claimed is:

1. An ultrasound treatment appliance having a handpiece with a built-in ultrasonic transducer, and an elongated probe extending forward from the handpiece and connected to said ultrasonic transducer in order to propagate ultrasonic vibrations, comprising:

a distal probe part formed as an integral part of or independently of said probe at the distal end of said probe;

a jaw opposed to said distal probe part so that the jaw can open or close freely; and a thin chip or elastic member, included in said jaw, for minimizing a sound stemming from vibrations propagated from said distal probe part, wherein said jaw is composed of a supporting portion and clamping portion.

2. An ultrasonic treatment appliance according to claim 1, wherein said thin chip is located on the clamping side of said clamping portion of said jaw on which said clamping portion touches a living tissue.

3. An ultrasonic treatment appliance according to claim 2, wherein said clamping portion is press-fitted into and thus fixed to said supporting portion.

4. An ultrasonic treatment appliance according to claim 3, wherein said thin chip is fitted into grooves bored on both sides of the bottom of a clamping ditch formed in said clamping portion, and thus locked.

5. An ultrasonic treatment appliance according to claim 3, wherein said thin chip is formed as an integral part of said clamping portion made of a resin material by performing insert molding.

6. An ultrasonic treatment appliance according to claim 3, wherein said thin chip is locked in said jaw by fixing said clamping portion to said supporting portion.

7. An ultrasonic treatment appliance according to claim 1, wherein said thin chip is made of a metallic material.

8. An ultrasonic treatment appliance according to claim 7, wherein the thickness of said thin chip ranges from 0.05 mm to 0.5 mm.

9. An ultrasonic treatment appliance according to claim 7, wherein the clamping surface of said thin chip on the treatment side thereof and the surface of said distal probe part coming into contact with the clamping surface are polished.

10. An ultrasonic treatment appliance according to claim 1, wherein said thin chip is made of a ceramic material.

11. An ultrasonic treatment appliance according to claim 10, wherein the thickness of said thin chip ranges from 0.05 mm to 0.5 mm.

12. An ultrasonic treatment appliance according to claim 10, wherein the thickness of said thin chip ranges from 0.1 mm to 0.3 mm.

13. An ultrasonic treatment appliance according to claim 10, wherein the surface of said distal probe part that meets the clamping surface of said thin chip on the treatment side thereof is coated with a ceramic.

14. An ultrasonic treatment appliance according to claim 1, wherein said thin chip is affixed and thus locked on the clamping side of said jaw.

15. An ultrasonic treatment appliance according to claim 1, wherein said thin chip is locked on the clamping side of said jaw using an adhesive and screw.

16. An ultrasonic treatment appliance according to claim 1, wherein said thin chip is fitted into grooves bored on both sides of the bottom of a clamping ditch, and thus locked.

17. An ultrasonic treatment appliance according to claim 1, wherein said clamping portion is fixed to said supporting portion using a screw.

18. An ultrasonic treatment appliance according to claim 1, wherein said clamping portion is freely attachable to or detachable from said supporting portion.

19. An ultrasonic treatment appliance according to claim 1, wherein said elastic member is interposed between said supporting portion and clamping portion of said jaw.

20. An ultrasonic treatment appliance according to claim 19, wherein said elastic member is a rubber member.

21. An ultrasonic treatment appliance according to claim 19, wherein said elastic member is a blade spring.

22. An ultrasonic treatment appliance according to claim 19, wherein said clamping portion and elastic member are molded in one united body.

23. An ultrasonic treatment appliance according to claim 22, wherein said elastic member is freely attachable to or detachable from said supporting portion.

24. An ultrasonic treatment appliance according to claim 19, wherein a quantity of contraction of said elastic member is set according to the property of said distal probe part on a quantity of deflection.

25. An ultrasonic treatment appliance according to claim 24, wherein the thickness of said elastic member changes between the distal portion and proximal portion thereof.

26. An ultrasonic treatment appliance according to claim 1, wherein said distal probe part has an ultrasonic treatment surface that is a flat surface parallel to the longitudinal-axis direction of said probe, and the section modulus of said distal probe part is larger on the proximal side thereof than on the distal side thereof.

27. An ultrasonic treatment appliance according to claim 26, wherein said section modulus of said distal probe part increases continuously from the distal side thereof to the proximal side thereof.

28. An ultrasonic treatment appliance according to claim 27, wherein said distal probe part has a surface along which the section modulus of said distal probe part varies continuously and linearly from the distal side thereof to the proximal side thereof.

29. An ultrasonic treatment appliance according to claim 27, wherein said distal probe part has a surface along which the section modulus of said distal probe part varies continuously and curvedly from the distal side thereof to the proximal side thereof.

30. An ultrasonic treatment appliance, comprising:
 an ultrasonic transducer for generating ultrasonic vibrations;
 a handpiece having said ultrasonic transducer incorporated therein;
 a probe connected to said ultrasonic transducer and serving as a vibration propagation member for propagating ultrasonic vibrations to a distal probe part that is a constituent part of a treatment assembly;
 a jaw, opposed to said distal probe part, being a constituent part of said treatment assembly; and
 a jaw supporting base having said jaw pivot freely,
 wherein said jaw supporting base is positioned according to a node of vibrations propagating along said probe and includes a restraining detent member for restraining said jaw supporting base and probe from rotating about the axes thereof so that said jaw and probe can be rotated together.

31. An ultrasonic treatment appliance according to claim 30, wherein said jaw supporting base is mounted in a sheath put on said probe with the rotation about the axis thereof restrained.

32. An ultrasonic treatment appliance according to claim 31, wherein an operating means for rotating said sheath is included in an operation unit.

33. An ultrasonic treatment appliance according to claim 30, wherein a plurality of surface finishing layers is overlaid on at least part of said probe that propagates ultrasonic vibrations.

34. An ultrasonic treatment appliance according to claim 33, wherein said probe is made of a titanium alloy, and a surface finishing layer is formed on the surface of the titanium alloy according to the PVD.

35. An ultrasonic treatment appliance according to claim 33, wherein said surface finishing layer is overlaid three times, and the total thickness of the three overlaid surface finishing layers is approximately 8 $\mu$m.

36. An ultrasonic treatment appliance according to claim 33, wherein said surface finishing layer to be formed on said probe is laid on a portion of said probe that may meet another member.

37. An ultrasonic treatment appliance according to claim 33, wherein an area to be coated with said surface finishing layer is narrower on an upper layer than on a lower layer.

38. An ultrasonic treatment appliance according to claim 37, wherein said area to be coated with said surface finishing layer gets narrowed gradually from a lowermost layer to an uppermost layer.

39. An ultrasonic treatment appliance according to claim 33, wherein an intermediate layer of said surface finishing layer except an uppermost layer serving as a surface is a plating layer.

40. An ultrasonic treatment appliance according to claim 30, wherein said distal probe part has an ultrasonic treatment surface that is a flat surface parallel to the longitudinal-axis direction of said probe, and the section modulus of said distal probe part is larger on the proximal side thereof than on the distal side thereof.

41. An ultrasonic treatment appliance according to claim 40, wherein the section modulus of said distal probe part increases continuously from the distal side thereof to the proximal side thereof.

42. An ultrasonic treatment appliance according to claim 41, wherein said distal probe part has a surface along which the section modulus of said distal probe part varies continuously and linearly from the distal side thereof to the proximal side thereof.

43. An ultrasonic treatment appliance according to claim 41, wherein said distal probe part has a surface along which the section modulus of said distal probe part varies continuously and curvedly from the distal side thereof to the proximal side thereof.

44. An ultrasonic treatment appliance, comprising:

an ultrasonic transducer for generating ultrasonic vibrations;

a handpiece having said ultrasonic transducer incorporated therein;

a probe connected to said ultrasonic transducer and serving as a vibration propagation member for propagating ultrasonic vibrations to a distal probe part that is a constituent part of a treatment assembly;

a jaw, opposed to said distal probe part, being a constituent part of said treatment assembly;

an operation rod coupled with the tip of said jaw and serving as an operation force conveying medium member for opening or closing said jaw;

a sheath for covering said probe and operation rod; and spacers for positioning said probe relatively to said operation rod in said sheath, wherein said spacers are loosely engaged with said probe and held by said operation rod so that said spacers will not be displaced in a longitudinal direction.

45. An ultrasonic treatment appliance according to claim 44, wherein at least part of said spacers are made of a material ensuring high sliding efficiency relative to said probe.

46. An ultrasonic treatment appliance according to claim 44, wherein said spacers are arranged at positions on said probe coincident with nodes of ultrasonic vibrations.

47. An ultrasonic treatment appliance according to claim 1, wherein a plurality of surface finishing layers are overlaid on at least part of said probe that propagates ultrasonic vibrations.

48. An ultrasonic treatment appliance according to claim 47, wherein said probe is made of a titanium alloy, and a surface finishing layer is formed on the surface of the titanium alloy according to the PVD.

49. An ultrasonic treatment appliance according to claim 47, wherein said surface finishing layer is overlaid three times, and the total thickness of the three overlaid surface finishing layers is approximately 8 μm.

50. An ultrasonic treatment appliance according to claim 47, wherein said surface finishing layer to be formed on said probe is laid on a portion of said probe that may meet another member.

51. An ultrasonic treatment appliance according to claim 47, wherein an area to be coated with said surface finishing layer is narrower on an upper layer than on a lower layer.

52. An ultrasonic treatment appliance according to claim 51, wherein said area to be coated with said surface finishing layer gets narrowed gradually from a lowermost layer to an uppermost layer.

53. An ultrasonic treatment appliance according to claim 47, wherein an intermediate layer of said surface finishing layer except an uppermost layer serving as a surface is a plating layer.

54. An ultrasonic treatment appliance according to claim 44, wherein a plurality of surface finishing layers is overlaid on at least part of said probe that propagates ultrasonic vibrations.

55. An ultrasonic treatment appliance according to claim 44, wherein said probe is made of a titanium alloy, and a surface finishing layer is formed on the surface of the titanium alloy according to the PVD.

56. An ultrasonic treatment appliance according to claim 54, wherein said surface finishing layer is overlaid three times, and the total thickness of the three overlaid surface finishing layers is approximately 8 μm.

57. An ultrasonic treatment appliance according to claim 54, wherein said surface finishing layer to be formed on said probe is laid on a portion of said probe that may meet another member.

58. An ultrasonic treatment appliance according to claim 54, wherein an area to be coated with said surface finishing layer is narrower on an upper layer than on a lower layer.

59. An ultrasonic treatment appliance according to claim 58, wherein said area to be coated with said surface finishing layer gets narrowed gradually from a lowermost layer to an uppermost layer.

60. An ultrasonic treatment appliance according to claim 54, wherein an intermediate layer of said surface finishing layer except an uppermost layer serving as a surface is a plating layer.

61. An ultrasonic treatment appliance according to claim 44, wherein said distal probe part has an ultrasonic treatment surface that is a flat surface parallel to the longitudinal-axis direction of said probe, and the section modulus of said distal probe part is larger on the proximal side thereof than on the distal side thereof.

62. An ultrasonic treatment appliance according to claim 61, wherein the section modulus of said distal probe part increases continuously from the distal side thereof to the proximal side thereof.

63. An ultrasonic treatment appliance according to claim 62, wherein said distal probe part has a surface along which the section modulus of said distal probe part varies continuously and linearly from the distal side thereof to the proximal side thereof.

64. An ultrasonic treatment appliance according to claim 62, wherein said distal probe part has a surface along which the section modulus of said distal probe part varies continuously and curvedly from the distal side thereof to the proximal side thereof.

* * * * *